(12) United States Patent
Maniar

(10) Patent No.: US 11,583,552 B2
(45) Date of Patent: Feb. 21, 2023

(54) PHARMACEUTICAL FORMULATION OF ARSENIC TRIOXIDE

(71) Applicant: Manoj Maniar, Fremont, CA (US)

(72) Inventor: Manoj Maniar, Fremont, CA (US)

(*) Notice: Subject to any disclaimer, the term of this patent is extended or adjusted under 35 U.S.C. 154(b) by 0 days.

(21) Appl. No.: 17/410,900

(22) Filed: Aug. 24, 2021

(65) Prior Publication Data

US 2022/0257647 A1    Aug. 18, 2022

Related U.S. Application Data

(60) Provisional application No. 63/150,556, filed on Feb. 17, 2021.

(51) Int. Cl.
*A61K 33/36* (2006.01)
*A61K 9/48* (2006.01)

(52) U.S. Cl.
CPC .............. *A61K 33/36* (2013.01); *A61K 9/485* (2013.01); *A61K 9/4833* (2013.01)

(58) Field of Classification Search
None
See application file for complete search history.

(56) References Cited

U.S. PATENT DOCUMENTS

| | | | |
|---|---|---|---|
| 672,335 A | 4/1901 | Smith | |
| 5,071,643 A * | 12/1991 | Yu | A61K 9/4866 424/455 |
| 5,200,191 A | 4/1993 | Steele et al. | |
| 6,340,473 B1 | 1/2002 | Tanner et al. | |
| 7,521,071 B2 | 4/2009 | Kumana et al. | |
| 8,394,422 B2 | 3/2013 | Alix et al. | |
| 10,092,595 B2 | 10/2018 | Kwong | |
| 10,111,836 B2 | 10/2018 | Vaddi et al. | |
| 10,493,099 B2 | 12/2019 | Eutick | |
| 10,653,628 B2 | 5/2020 | Vaddi et al. | |
| 2008/0089949 A1 | 4/2008 | Kwong | |
| 2010/0291234 A1* | 11/2010 | Kwong | A61P 19/02 435/375 |
| 2011/0091573 A1 | 4/2011 | Warrell, Jr. et al. | |
| 2015/0359810 A1 | 12/2015 | MacBeth et al. | |
| 2020/0060974 A1 | 2/2020 | Vaddi et al. | |
| 2020/0345770 A1 | 11/2020 | Mathews et al. | |

FOREIGN PATENT DOCUMENTS

| | | |
|---|---|---|
| EP | 0293406 B1 | 9/1991 |
| EP | 3106169 B1 | 5/2021 |
| WO | 8403416 A1 | 9/1984 |
| WO | 2022180582 A1 | 9/2022 |

OTHER PUBLICATIONS

Kumana, C., et al. "Systemic availability of arsenic from oral arsenic-trioxide used to treat patients with hematological malignancies." European journal of clinical pharmacology 58.8 (2002): 521-526. (Year: 2002).*

Awad, Atheer, et al. Chapter 20—Liquid dosage forms, Editor(s): Adeboye Adejare, Remington (Twenty-third Edition), Academic Press, available online Nov. 13, 2020, pp. 359-379, https://doi.org/10.1016/B978-0-12-820007-0.00020-9. (Year: 2020).*

Gullapalli, Rampurna Prasad. "Soft gelatin capsules (softgels)." Journal of pharmaceutical sciences 99.10 (2010): 4107-4148. (Year: 2010).*

"Arsenic Trioxide", Chemistry: LibraText Online, Website <https://chem.libretexts.org/Under_Construction/Stalled_Project_(Not_under_Active_Development)/Walker/Chemicals/Substance_A/Arsenic_trioxide>, Updated Jun. 15, 2019, 1 page.

"Arsenic Trioxide", Hazardous Substance Fact Sheet, NJ Health Department of Health, Website <https://www.nj.gov/health/eoh/rtkweb/documents/fs/0161.pdf>, Revision: Jan. 2010, p. 1-6.

Budavaris et al, "Arsenic Trioxide" The Merck Index. An encyclopedia of chemicals, drugs and biologicals, NJ: Merck & Co. Inc., 1989, Monograph 832, p. 127.

Gullapalli, Review, Soft Gelatin Capsules (Softgels), Journal of Pharmaceutical Sciences, 2010, vol. 99, 10: 4107-4148.

Kumana et al., "Resurrection of Oral Arsenic Trioxide for Treating Acute Promyelocytic Leukaemia: A Historical Account From Bedside to Bench to Bedside", Frontiers in Oncology, 2020, vol. 10, Article 1294: 1-7.

Levander et al, "Arsenic, Medical and Biological Effects of Environmental Pollutants" Textbook, Committee on Medical and Biological Effects of Environmental Pollutants, National Academy of Sciences, 1977, p. 1-340.

"Medsenic Announces Positive Results of its Phase II Clinical Study with Arscimed® for the Treatment of Chronic Graft Versus Host Disease (cGvHD)", Website <https://www.businesswire.com/news/home/20210329005475/en/Medsenic-Announces-Positive-Results-of-its-Phase-II-Clinical-Study-with-Arscimed%C2%AE-for-the-Treatment-of-Chronic-Graft-Versus-Host-Disease-cGvHD>, issued on Mar. 29, 2021, pp. 1-4.

Zhu et al, "Oral Tetra-Arsenic Tetra-Sulfide Formula Versus Intravenous Arsenic Trioxide as First-Line Treatment of Acute Promyelocytic Leukemia: A Multicenter Randomized Controlled Trial", Journal of Clinical Oncology, 2013, vol. 31, 33: 4215-4222.

International Search Report and Written Opinion for PCT/US22/016529 dated Jul. 7, 2022, 11 pages.

Awad, A., Madla, C.M., Gavins, F.K., Allahham, N., Trenfield, S.J., & Basil, A.W. (2021). Liquid dosage forms. Remington.

(Continued)

*Primary Examiner* — Bethany P Barham
*Assistant Examiner* — Peter Anthopolos
(74) *Attorney, Agent, or Firm* — Veritay Group IP PLLC; Susan B. Fentress; Liam O'Donnell

(57) ABSTRACT

Liquid fill matrices comprising dissolved arsenic trioxide and having not more than 20% aqueous component and at least 80% nonaqueous component, wherein the components are miscible, are described as well as processes of preparing such liquid fill matrices and processing the liquid fill matrices into dosage forms including soft capsules; for the treatment of various ailments, such as cancer and GVHD.

14 Claims, 2 Drawing Sheets

(56) References Cited

OTHER PUBLICATIONS

Kumana, C.R., Au, W.Y., Lee, N., Kou, M., Mak, R., Lam, C.K., & Kwong, Y. (2002). Systemic availability of arsenic from oral arsenic-trioxide used to treat patients with hematological malignancies. European Journal of Clinical Pharmacology, 58, 521-526.

Raj, Abhishek, Soft Gelatin Capsules (Softgels)., Pharma Tutor, Oct. 1, 2015, 16-18, (3).

Ravandi et al., Oral arsenic trioxide ORH-2014 pharmacokinetic and safety profile in patients with advanced hematologic disorders. Haematologica. Jun. 2020;105(6):1567-1574. Epub Sep. 26, 2019.

Rytting E, Lentz KA, Chen XQ, Qian F, Venkatesh S. A quantitative structure-property relationship for predicting drug solubility in PEG 400/water cosolvent systems. Pharm Res. Feb. 2004;21(2):237-44.

\* cited by examiner

PHARMACEUTICAL FORMULATION OF ARSENIC TRIOXIDE

CROSS-REFERENCE TO RELATED APPLICATIONS

This Nonprovisional application claims priority under 35 U.S.C. § 119(e) on U.S. Provisional Application No. 63/150,556 filed on Feb. 17, 2021, and on Provisional Application No. 202141011250 filed on Mar. 17, 2021 in India, the contents of each of which are hereby incorporated by reference in its entirety.

FIELD OF THE INVENTION

The invention relates to safer oral pharmaceutical formulation of the highly toxic drug Arsenic Trioxide. The oral pharmaceutical formulation is a solid oral dosage form comprising Arsenic Trioxide in dissolved form. The dosage form is a soft capsule filled with a liquid fill matrix containing Arsenic Trioxide in dissolved form. The shell of the soft capsules has traditionally been made using animal-based gelatin, but they could be of plant-based alternatives ranging from a variety of seaweed-based alternatives to modified starch. Since Arsenic Trioxide is in dissolved form and since there is no direct contact with Arsenic Trioxide, each step from manufacturing to packing and administration is extremely safe. The soft capsule having dissolved Arsenic Trioxide resolves all issues of solubility, bioavailability and homogeneity; as encountered with a traditional oral pharmaceutical formulation such as tablets and capsules filled with a powder. Thus, soft capsules, with the active Arsenic Trioxide in a solution state, tends to be the most efficient oral drug delivery system.

Capsule can be made available in multiple strengths as per the indications.

OBJECTS OF THE INVENTION

A first object of the present invention is to provide a solid oral dosage form in the form of a soft gelatin capsules or vegan soft capsules containing dissolved Arsenic Trioxide. The dissolved form of Arsenic Trioxide in liquid fill matrix resolves various issues of solubility and therefore bioavailability of Arsenic Trioxide after ingestion.

A second object of the invention is to provide various fill matrices containing Arsenic Trioxide in dissolved form for encapsulating into a soft capsule.

A third object of the present invention is to provide a process to manufacture a fill matrix containing Arsenic Trioxide in dissolved form which is suitable for encapsulation into a soft capsule using traditional methods.

The fourth object of the invention is to provide a safer oral pharmaceutical formulation of Arsenic Trioxide. Manufacturing such pharmaceutical formulation is simple, safer, and cost effective compared to any formulation wherein Arsenic Trioxide is in solid oral form in a final formulation. Consuming formulations of the present invention prevents accidental contact with highly toxic Arsenic Trioxide.

A fifth object of the invention is to provide a pharmaceutical formulation of Arsenic Trioxide which can be self-administered. No hospitalization is necessary for the administration, and it can be handled with ease by the patient as well as caregiver and is therefore patient compliant.

Yet one more object of the present invention is to provide a method for treating cancer or condition mediated by abnormal cell proliferation or method of treating chronic Graft versus Host Disease by administering to the patient the solid oral pharmaceutical formulation containing Arsenic Trioxide dissolved in a liquid matrix. The cancer or abnormal cell proliferation condition is selected from Acute promyelocytic leukemia (APL), Myelodysplastic Syndromes, Acute myeloblastic leukemia (AML), and Multiple Myeloma.

DESCRIPTION OF CERTAIN TERMS

OSHA: Occupational Safety and Health Administration, United States Department of Labor;

NIOSH: The National Institute for Occupational Safety and Health (NIOSH), Centers for Disease Control And Prevention;

ACGIH: American Conference of Governmental Industrial Hygienists;

IDLH: Immediately dangerous to life or health defined by the US National Institute for Occupational Safety and Health (NIOSH).

BACKGROUND OF THE INVENTION

Arsenic compounds and particularly Arsenic Trioxide are gaining therapeutic importance for remedial effects on various diseases. Arsenic Trioxide has been indicated for induction of remission and consolidation in patients with acute promyelocytic leukemia (APL) who are refractory to, or have relapsed from, retinoid and anthracycline chemotherapy, and whose APL is characterized by one or more acquired changes (mutations) to the DNA of a single blood-forming cell. APL cells have a very specific abnormality that involves chromosomes 15 and 17, leading to the formation of an abnormal fusion gene PML/RARα. This mutated gene causes many of the features of the disease.

The commonly used chemotherapy drug All trans retinoic acid (ATRA) for treating cancer is also used in the treatment of APL. However, ATRA as a single agent is not highly effective because it does not directly kill malignant cell. Hence, ATRA in combination with Arsenic Trioxide is administered to APL patients. The treatment modality is the daily administration of solution of Arsenic Trioxide intravenously over 2-4 hours over a period several months.

Similarly, Arsenic Trioxide is known to be an effective treatment for AML and is also being investigated for efficacy in treating refractory cancer patients harboring TP53 mutations, hepatocellular carcinoma, NPM1 mutations in AML, neuroblastoma, metastatic ovarian and endometrial cancer, HIV-1, myelodysplastic syndrome (MDS), Multiple Sclerosis (MS) and more. The current treatment modality involves daily administration of intravenous infusion over 1-4 hours depending upon the disease state for months at a time.

U.S. Pat. No. 6,723,351 mentions that Arsenic Trioxide can be used against a variety of leukemias, including but not limited to: Acute lymphoblastic leukemia (ALL), Acute lymphoblastic B-cell leukemia, Acute lymphoblastic T-cell leukemia, Acute myeloblastic leukemia (AML), Chronic myelocytic leukemia (CML), etc.

US 2008/0089949 discloses the use of Arsenic Trioxide for the treatment of cancers that are dependent on Cyclin D1. Specifically, the application discloses the use of oral Arsenic Trioxide for the treatment of patients with Mantle Cell Lymphoma.

U.S. Pat. No. 8,394,422 discloses a method for treating and/or preventing autoimmune and/or inflammatory diseases, including the graft-versus-host disease, comprising administering to a patient in need thereof, a therapeutically effective amount of an arsenic compound or a pharmaceutically acceptable salt.

U.S. Pat. No. 10,092,595 discloses methods for treating or preventing one or more symptoms of rheumatoid arthritis or other types of inflammatory arthritis involves administering a formulation containing an effective amount of Arsenic Trioxide to an affected patient.

Recently, positive results were announced with Arsenic Trioxide IV injection formulation from a clinical study for chronic Graft versus Host disease (Loyer Annie-Florence, Mar. 29, 2021). Hence, with ongoing interest and new clinical studies on Arsenic Trioxide, its therapeutic value is increasing day by day.

Although Arsenic Trioxide is gaining importance, its formulations reported in the art are still limited and have a lot of drawbacks. It is extremely difficult to handle and process this toxic drug into suitable safer pharmaceutical formulations. Accidental ingestion of Arsenic Trioxide can be fatal. It causes severe digestive tract burns with abdominal pain, vomiting, and possible death. Ingestion of arsenic compounds can produce convulsions, coma, and possibly death within 24 hours. Its inhalation may cause severe irritation of the respiratory tract with sore throat, coughing, shortness of breath and delayed lung edema. Inhalation of arsenic compounds may lead to irritation and to possible nasal perforation. Long-term exposure to arsenic compounds may produce impairment of peripheral circulation. (Arsenic Trioxide-Hazardous substance Factsheet by New Jersey Department of Health, 2010).

Currently, Arsenic Trioxide is available as a sterile injectable solution dosage form. It is administered via an intravenous (IV) injection over the course of one or two hours. This may be extended up to four hours if the patient has a vasomotor reaction. This also means that patient cannot self-administer the dose and a caregiver is required for its safe administration. Also, admission into an out-patient clinic or hospital is necessary for the administration.

To overcome the limitations of the injectable formulation, attempts have been made to develop an oral formulation of Arsenic Trioxide. Oral formulations are disclosed in a U.S. Pat. No. 7,521,071 B2 and a European Patent EP 3106169 B1. For example, European Patent EP 3106169 B1 teaches preparation of Arsenic Trioxide oral solution for use in the treatment of non-Hodgkin's lymphomas by oral administration. Process of preparing 1 mg/ml oral solution of Arsenic Trioxide is disclosed therein. According to the reported process, Arsenic Trioxide is suspended in sterile water and dissolved by addition of 3M Sodium hydroxide. pH is adjusted by 6M hydrochloric acid or dilute HCl acid to around 7.2 to obtain a final aqueous solution of the concentration 1 mg/ml.

Another prior art (Table 5 of U.S. Pat. No. 10,111,836 B2) provides a more concentrated solution of Arsenic Trioxide. A 30 ml solution having 1000 mg of Arsenic Trioxide and 500 mg of sodium hydroxide represents 33.3 mg/ml aqueous solution.

Kumana C. R. et al (Kumana CR et al., 2020) reported first time the preparation of 1 mg/ml oral-Arsenic Trioxide solution that had comparable bioavailability to intravenous injection of Arsenic Trioxide and achieved considerably higher intracellular arsenic concentrations than the corresponding plasma values. The safety, tolerability and clinical efficacy of the oral solution (1 mg/ml) was confirmed in long-term follow-up studies.

However, according to the dose, caregiver or patient needs to measure oral solution before administration. Oral solution although can be self-administered, patients, caregivers and family members are always at risk of coming in contact with the hazardous Arsenic Trioxide. Solution dosage form does not avoid risk of contact of Arsenic Trioxide with skin, eyes, and other body parts by accident. Repeated exposure during each dose can be dangerous.

Another oral form of Arsenic is Realgar/Indigo naturalis (RIF). RIF is a tablet dosage form. One pill of RIF is 270 mg which contains 30 mg of Realgar, 125 mg of Indigo naturalis, 50 mg of Radix salviae miltiorrhizae, 45 mg of Radix pseudostellariae, and 20 mg of garment film. It was approved for medical use in China in 2009. It contains realgar which is tetra-arsenic tetra-sulfide. It is considered similar in effectiveness to Arsenic Trioxide (Hong-Hu Zhuet al, 2013).

Prior arts mentioned tablets and capsule formulations of Arsenic Trioxide, manufacturing of these forms is unsafe and extremely difficult. Several processes like blending, compaction or granulation, milling, drying, dry milling/sizing and tablet compression or capsule filing generate lot of fine particles and dust in the air and inhaling such air is extremely hazardous.

U.S. Pat. Nos. 10,111,836 B2 and 10,653,628 B2 discloses orally administrable lyophilized compositions of Arsenic Trioxide and a method for lyophilizing the Arsenic Trioxide solution. The patent addresses the solubility issues of Arsenic Trioxide and reports several experiments conducted to dissolve Arsenic Trioxide including using. i) cyclodextrin, ii) sodium lauryl sulphate; iv) Tween 80; v) isopropyl alcohol; vi) ethanol; vii) sodium bicarbonate vii) poloxamer; viii) sodium hydroxide. However, none of these could dissolve Arsenic Trioxide except sodium hydroxide in a specified proportion. Since ethanol, isopropyl alcohol, SLS, Tweens, cyclodextrin, poloxamer etc. could not dissolve Arsenic Trioxide, it is apparent that most commonly used solubilizing agents do not solubilize Arsenic Trioxide. The most preferred ingredient that was reported for solubilizing Arsenic Trioxide was sodium hydroxide for which an aqueous solution is needed. Solubility of Arsenic Trioxide thus mandates use of an aqueous solution. One of the exemplary trial discloses that an amount of 500 mg of sodium hydroxide is required to dissolve 1000 mg of Arsenic Trioxide in 30 ml water.

The final method disclosed involves solubilizing Arsenic Trioxide with an alkalizing agent (such as sodium hydroxide) followed by titrating with a low concentration acid (such as hydrochloric acid). The solubilized mixture is stirred and then lyophilized. The collected lyopremix is then sifted, blended with excipients/lubricants, and encapsulated in hard gelatin capsules.

There are many disadvantages of this method. For example, lyophilization process proposed in this patent involves three stages—freezing of the solution, primary drying of the frozen solution followed by secondary drying to obtain the cake. Overall, this process would take several days to achieve dry powder cake. At higher scale, this manufacturing process is error-prone and cost prohibitive. Additionally, this dry powder cake may be prone to moisture absorption making it harder for further processing of the material. Moisture absorption in the dry powder could potentially hinder the automated process of filling powder blend in capsules and may impact the disintegration and dissolution. Also, the sifting and dry blending process with other excipients can introduce airborne Arsenic Trioxide-containing particles, which can harm manufacturing personnel and would require costly containment procedures.

U.S. Pat. No. 7,521,071 B2 reports that Arsenic Trioxide powder is sparingly and extremely slowly soluble in cold water; even in boiling water it is only soluble in a 1:15 ratio (Arsenic Trioxide. In: Budavari S O'Neil M J (Eds), The Merck Index. An encyclopedia of chemicals, drugs and biologicals. NJ: Merck & Co., Inc. 11th Ed., Rahway, N.J., USA. 1989. Monograph 832, p 127).

Chem.libretexts reports that Arsenic Trioxide is insoluble in alcohol, chloroform, and ether (see "Arsenic Trioxide" on the chem.libretexts website).

In a book titled "Arsenic Medical and Biological Effects of Environmental Pollutants (1977)" by National Research Council (US) Committee on Medical and Biological Effects of Environmental Pollutants provides data on solubility of Arsenic Trioxide in water according to which the solubility of Arsenic Trioxide in 100 g of water is 1.2 g at 0° C., 2.1 g at 25° C., and 5.6 g at 75° C. The rate of dissolution is very low, and several weeks are required to achieve equilibrium.

U.S. Pat. No. 10,493,099 B2 discloses the new salt form of Arsenic (Arsenic carbonate/bicarbonate) to address the poor solubility and low dissolution rates of Arsenic Trioxide. The new salts are formulated as a solid oral dosage form wherein the Arsenic salt is present in the solid state, blended with excipients and filled into a capsule.

Thus, it is extremely challenging to design oral formulations of Arsenic Trioxide which are patient compliant, prevent accidental exposure of arsenic to care giver, and safe to manufacture them.

There is a need in the art to develop a solid oral dosage form which can take care of all above shortcomings. The new dosage form should be such that it can be self-administered or administered by a caregiver without any risk of coming in contact with Arsenic Trioxide.

SUMMARY OF THE INVENTION

A first aspect of the present invention is to provide a solid oral dosage form in the form of a soft gelatin capsules or vegan soft capsules containing dissolved Arsenic Trioxide. The dissolved form of Arsenic Trioxide in liquid fill matrix resolves various issues of solubility, dissolution rate and therefore bioavailability of Arsenic Trioxide after ingestion. The different fill matrices of the present invention keep the Arsenic Trioxide in the dissolved state when exposed to either simulated gastric or intestinal fluid.

A second aspect of the invention is to provide various fill matrices containing Arsenic Trioxide in dissolved form. The liquid fill matrix comprises dissolved Arsenic Trioxide and at least 80% of a nonaqueous component wherein the Arsenic Trioxide is maintained in dissolved form. The non-aqueous component of the liquid fill matrix is predominantly hydrophilic but may contain some amount of nonhydrophilic component such as hydrophobic component. When both hydrophilic and hydrophobic components are employed, they are selected in such a way that they are miscible with one another.

The fill matrix of the invention can be administered to animals, including man, in any pharmaceutically acceptable manner, such as orally, rectally, pulmonary, intravaginally, locally (ointments or drops), transdermal, parenteral administration, intravenous, intraperitoneal, intramuscular, sublingual or as a buccal or nasal spray. The fill matrix can also be administered parenterally upon appropriate dilution with a diluent. The preferred diluent is aqueous with or without buffers and tonicity modifying agents. For aerosol administration, the fill matrix is mixed with the propellant which may include a carrier like lecithin or suitable surfactants.

The most preferred route of administration is oral wherein the fill matrix is encapsulated in either a hard or soft capsules. Accordingly, the second aspect of the invention provides various fill matrices containing Arsenic Trioxide in dissolved form for encapsulation into a soft capsule. Arsenic Trioxide is sparingly soluble and dissolves extremely slowly in water. A solubilizing agent preferably an alkalizing agent such as sodium hydroxide is used. It is preferably in the form of its aqueous solution. The soluble form of Arsenic Trioxide as disclosed in prior art are predominantly aqueous solutions which are not suitable for encapsulation into a soft capsule. In the present invention, the fill matrix having dissolved Arsenic Trioxide contains at least 80% nonaqueous component which contains one or more fill material and optionally a solvent or a cosolvent, and an antioxidant. Additionally, it may contain one or more of surfactants, absorption enhancers and crystal growth inhibitors. Not more than 20% of the fill matrix is aqueous and includes Arsenic Trioxide, a solubilizing agent and a neutralizing agent preferably in the form of their aqueous solutions. Sodium hydroxide and hydrochloric acid are respectively preferred solubilizing agent and neutralizing agent. Out of 80% of the nonaqueous component, amount of fill material is at least 60% of the fill matrix. The other 20% of nonaqueous component can be one or more of a solvent, a cosolvent, surfactant, absorption enhancer and crystal growth inhibitor. The nonaqueous component of the fill matrix is predominantly hydrophilic. One of the preferred fill materials is polyalkylene glycol such as for example, polyethylene glycol 400 or polyethylene glycol 600. However, Arsenic Trioxide has low solubility in polyethylene glycol. Hence, there always exists a concern of solubilizing Arsenic Trioxide in liquid fill matrix which includes at least 80% by weight a non-aqueous fill material like polyethylene glycol. Nevertheless, under this aspect, the invention provides fill matrices having Arsenic Trioxide in dissolved form without any apprehension of precipitation.

A third aspect of the present invention is to provide a process to manufacture the fill matrix containing Arsenic Trioxide in dissolved form which is suitable for encapsulation using traditional methods. Under this aspect, invention provides a certain order of mixing ingredients thereby avoiding discoloration of the fill matrix.

A fourth aspect of the invention is to provide a safer pharmaceutical formulation of Arsenic Trioxide which prevents direct contact to the hazardous Arsenic Trioxide by either the patient, caregiver or the manufacturing personnel. Manufacturing such pharmaceutical formulation is simpler, safer, and cost effective compared to any other oral formulation having Arsenic Trioxide in solid form. The manufacturing of fill matrix for encapsulation is very simple and done in closed tanks. The process employs minimal material and machine handling, loading and unloading, and equipment transfers.

A fifth aspect of the invention is to provide a pharmaceutical formulation of Arsenic Trioxide which can be self-administered. No hospitalization is necessary for the administration, and it can be handled with ease by the patient as well as caregiver and is therefore patient compliant. A soft capsule of the present invention is simply ingested with water. Hence, visiting out-patient clinics or hospitals is avoided. The soft capsule can be carried by the patient very conveniently such as to their workplace and therefore has a great patient compliance. The present invention not only provides a safer but also a more patient compliant treatment.

Yet one more aspect, the sixth aspect of the present invention is to provide a method of treating cancer or condition mediated by abnormal cell proliferation or a method of treating chronic Graft versus Host Disease in a patient in need thereof, comprising administering to the patient the solid oral pharmaceutical formulation, containing an effective amount of Arsenic Trioxide, comprising a liquid fill matrix wherein Arsenic Trioxide is present in dissolved form in the said liquid fill matrix and wherein the oral pharmaceutical formulation is a soft capsule encapsulating the liquid fill matrix.

DETAILED DESCRIPTION OF THE INVENTION

Figure 1:
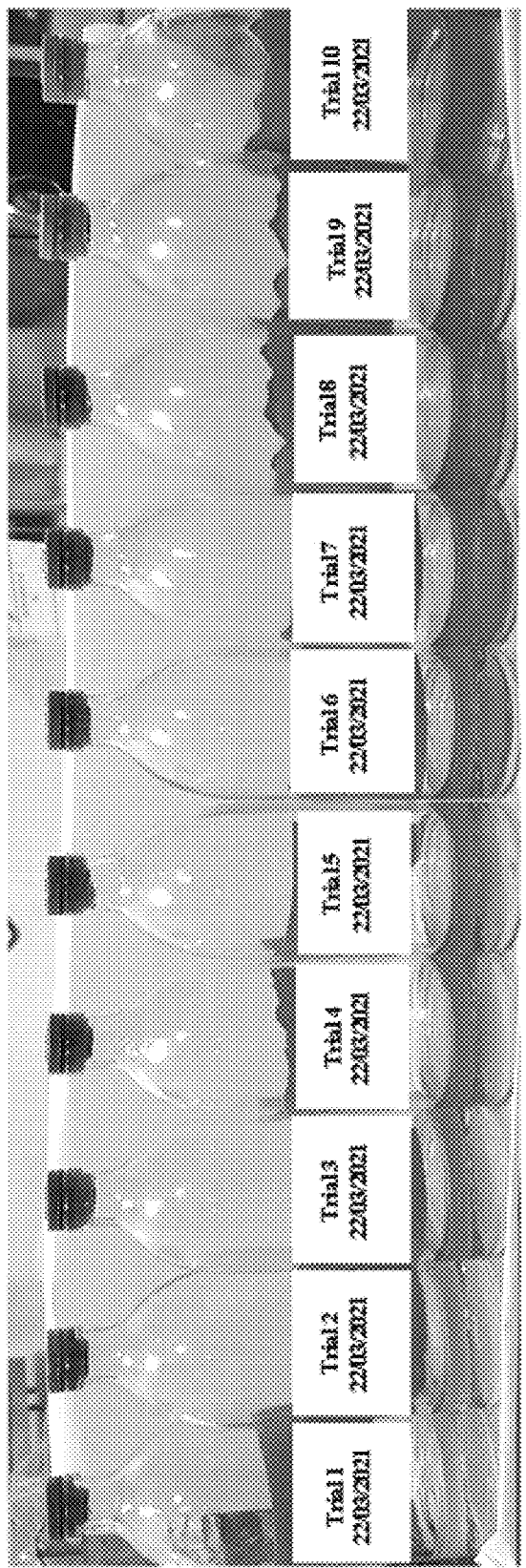
FIG. 1 provides discoloration produced after pretreating polyethylene glycol with sodium hydroxide which intensifies with higher amounts/concentrations of sodium hydroxide. This discoloration was observed during trials 11-20 of Example 2 before adding Arsenic Trioxide.

The present invention provides liquid fill matrix compositions of Arsenic Trioxide where Arsenic Trioxide is present in the dissolved form. The liquid fill matrix has at least 80% of the nonaqueous component. The fill matrix of the invention can be administered to animals, including man, in any pharmaceutically acceptable manner, such as orally, rectally, pulmonary, intravaginally, locally (ointments or drops), transdermal, parenteral administration, intravenous, intraperitoneal, intramuscular, sublingual or as a buccal or nasal spray. The fill matrix can be administered parenterally upon appropriate dilution with a diluent. The preferred diluent is aqueous with or without buffers and tonicity modifying agents. Buffers that can be employed include, but are not limited to, citrate, sodium phosphate, sodium bicarbonate and acetate. Tonicity modifying agents include, but are not limited to, sodium chloride, dextrose and mannitol. For aerosol administration, the fill matrix is mixed with the propellant hydrofluoroalkane such as 1,1,1,2-tetrafluoroethane or the like which may include a carrier like lecithin or suitable surfactants. The most preferred route of administration is oral wherein the fill matrix is encapsulated in either a hard or soft capsules. The invention preferably provides an oral pharmaceutical formulation of Arsenic Trioxide in the form of a solid oral dosage form. The said oral pharmaceutical formulation of Arsenic Trioxide comprises a liquid fill matrix wherein Arsenic Trioxide is present in dissolved form in the said liquid fill matrix and wherein the oral pharmaceutical formulation is a soft capsule encapsulating the liquid fill matrix.

The invention provides safer oral pharmaceutical formulation of Arsenic Trioxide which are self-administered or safely administered by a caregiver without any accidental exposure to toxic drug Arsenic Trioxide and without any need to get admitted to an out-patient clinic or hospital and hence the treatment is patient compliant. The invention provides soft capsules of Arsenic Trioxide. The soft capsules encapsulate a fill matrix having Arsenic Trioxide in dissolved form. The soft capsule form of Arsenic Trioxide and processes of preparation thereof are simple, safer, and cost effective. These oral pharmaceutical formulations are manufactured in closed tanks with minimum equipment handling and equipment transfers. Consuming Arsenic Trioxide formulation of the present invention is free of direct contact with Arsenic Trioxide. Presence of Arsenic Trioxide in dissolved form in liquid fill matrix resolves various issues of solubility and dissolution rates, and therefore does not impact bioavailability of Arsenic Trioxide after ingestion. The oral pharmaceutical formulations can deliver up to 100 mg of Arsenic Trioxide per day (q.i.d administration of a single capsule) or more.

Soft capsules as dosage forms have many advantages. They allow encapsulating poorly soluble drugs in liquid fill form. They are easy to swallow and aesthetically pleasing. The oxygen permeability is very low, and the inner fill matrix is well protected from degradation. Soft capsules are also free from odor and taste of components of the fill matrix. The hermetic seal and lack of headspace provides protection against atmospheric oxygen that may lead to degradation of APIs sensitive to oxidation. Properly designed shells rupture rapidly and then dissolve quickly in the gastrointestinal fluid, releasing the API from the liquid fill formulation and ensuring it remains solubilized throughout the gastrointestinal tract. Particularly in case of Arsenic Trioxide where the drug is in solution, completely encapsulated in either gelatin or vegetarian shell, manual handling of such soft capsules would not expose either the patient or caregiver to Arsenic.

Soft capsules of the present invention are preferably soft gelatin capsules and alternatively, vegan soft capsules. Vegan soft capsules are made from plant-based alternatives ranging from a variety of seaweed-based alternatives to modified starch.

Soft capsules volume may typically vary from around 0.15 ml to around 1.5 ml with 0.5 ml to 1 ml as one of the preferred size ranges. Volume of the fill matrix that can be incorporated in a soft capsule also slightly varies according to the shape of the soft capsule. Soft capsules are generally oblong or round, or oval in shape. An oblong soft capsule can contain a fill matrix from 0.142-0.185 cc/ml (size 3 oblong) to 1.232-1.478 cc/ml (size 24 oblong). A round soft capsule can contain a fill matrix from 0.046-0.062 cc (size 1 round) to 0.925-1.230 cc (size 20 round). An oval soft capsule can contain a fill matrix from 0.092-0.142-(size 2 oval) to 1.047-1.232 cc (size 20 oval).

There are other types such as tube soft capsules, suppository soft capsules etc. But oblong, oval and round are most routinely used as pharmaceutical dosage forms.

The present invention discloses an oral soft capsule pharmaceutical formulation comprising a liquid fill matrix having at least 80% of nonaqueous component and wherein Arsenic Trioxide is present in dissolved form in the said liquid fill matrix which is encapsulated in such soft capsule. Further the liquid fill matrix contains not more than 20% of the aqueous component.

The liquid fill matrix comprises dissolved Arsenic Trioxide and at least 80% of nonaqueous component.

The liquid fill matrix contains
(i) at least 80% of nonaqueous component and
(ii) not more than 20% of the aqueous component.

The non-aqueous component of the liquid fill matrix is predominantly hydrophilic and comprises fill material and one or more of solvent, cosolvent, surfactant, absorption enhancer and crystal growth inhibitor. The aqueous component comprises Arsenic Trioxide and solubilizing agent in suitable form. The aqueous and nonaqueous components are miscible forming the said liquid fill matrix.

Although non-aqueous component of the liquid fill matrix is predominantly hydrophilic, some of it may be replaced by a non-hydrophilic or hydrophobic component which may amount to a maximum of 20% of the nonaqueous component, and preferably to a maximum of 20% of the fill material. When both the hydrophilic component such as fill material, solvent, cosolvent etc. and the non-hydrophilic component are present, they are miscible with one another.

The fill material is preferably a polyalkylene glycol and more preferably a polyethylene glycol such as PEG 200, PEG 300, PEG 400, PEG 600, PEG 800 and PEG 1000 and any combination thereof. Fill materials also may comprise of various poloxamers, ethanol, dimethyl isosorbide, TRANSCUTOL™, solubilizers with common brand name Gelucire and Labrafil having HLB values of 7 and above including but not limited to Gelucire 44/14 which is Lauroyl Polyoxyl-32 glycerides/Lauroyl Macrogol-32 glycerides, Gelucire 50/13 which is Stearoyl polyoxyl-32 glycerides or Stearoyl macrogol-32 glycerides, Gelucire 48/16 which is Polyethylene glycol monostearate and LABRAFIL® M1944 CS which is Oleoyl macrogol-6 glycerides/Oleoyl polyoxyl-6 glycerides and LABRAFIL® M 2125 CS which is Linoleoyl polyoxyl-6 glycerides NF/Linoleoyl macrogol-6 glycerides.

Additionally, fill matrix may comprise of one or more further solvents selected from benzyl alcohol, ethylene glycol phenyl ether, propylene glycol, propylene glycol phenyl ether, propylene carbonate, phenoxyethanol, dimethyl malonate, dimethyl succinate, diethyl succinate, dibutyl succinate, TRANSCUTOL™ P, dimethyl glutarate, diethyl glutarate, dibutyl glutarate, dimethyl adipate, diethyl adipate, and dibutyl adipate.

Additionally, the nonaqueous component may contain one or more hydrophobic components such as essential oils and carrier oils such as olive oil.

Fill material is preferably polyalkylene glycol. The most preferred fill material is polyethylene glycol. Various grades of polyethylene glycol can be employed alone or in combination with other grades and include PEG 200, PEG 300, PEG 400, PEG 600, PEG 800, PEG 1000 etc.

Preferably, a solubilizing agent is an alkalizing agent. An alkalizing agent can be one or more selected from barium hydroxide, sodium hydroxide, potassium hydroxide, sodium metasilicate, calcium hydroxide, trisodium phosphate, potassium carbonate, sodium carbonate, ammonium hydroxide, diethylamine, triethylamine, tromethamine, picoline, dicyclohexylamine, N,N'-dibenzyl-ethylenediamine, and amino acids including arginine, lysine and glycine, and their salts. Preferred alkalizing agents are potassium hydroxide and sodium hydroxide.

Preferred fill material is polyalkylene glycol such as polyethylene glycol. Preferred solubilizing agent is sodium hydroxide used as an aqueous solution which is optionally partially neutralized by means of a neutralizing agent. Trials with and without neutralization are successfully conducted.

Preferably a neutralizing agent is an acid selected from organic and inorganic acids and is preferably selected from sulfuric acid, carbonic acid, phosphoric acid, nitric acid, hydrochloric acid, hydrobromic acid, hydrofluoric acid, Boric acid, acetic acid, citric acid, ascorbic acid, lactic acid, acetylsalicylic acid, oxalic acid, Ethylenediamine tetra acetic acid, malic acid, Tartaric acid. The most preferred neutralizing agent is hydrochloric acid.

The invention provides a dose from 0.1 mg to 25 mg of Arsenic Trioxide per unit dosage form which is prepared by employing the liquid fill matrix of the present invention. Generally, as the dose is higher, the amount of nonaqueous component reduces and the amount of aqueous component increases; and as the dose is reduced, the amount of nonaqueous component increases and the amount of aqueous component reduces. Within the nonaqueous component, fill material increases as the dose reduces, and fill material decreases as the dose increases. Therefore, for a 25 mg dose, the nonaqueous component will be closer to 80% but for the 0.1 mg dose, the nonaqueous component will be much higher than 80% and can be higher than 90%, 95% and even 99% of the fill matrix. Therefore, generally when the dose of Arsenic Trioxide is high, amounts of both aqueous component and cosolvent are higher and amount of fill material is lower than the respective amounts for lower dose.

However, it is also possible that different strengths of dosage form incorporating different doses have the same amount of aqueous and nonaqueous components. This is possible when compositions are made dose weight proportional which means it is possible to change doses by merely incorporating different volumes of the same composition in different sized capsules.

Both the above methods viz. method 1 where aqueous and nonaqueous component vary with the dose and method 2 where the amounts are same for a certain dose range are provided under tables 2, 3 and 4. As seen from each of tables 2, 3 and 4, within a single table, dose weight proportional compositions can be prepared. However, when tables 2, 3 and 4 are considered together, while going from table 2 to 3 and 3 to 4, as dose reduces, aqueous component reduces and nonaqueous component increases and within the nonaqueous component as dose reduces, fill material increases and cosolvent reduces.

Irrespective of the dose and method adopted, an aqueous component is always maximum of 20% and the nonaqueous component is not less than 80% of the liquid fill matrix. Even though Arsenic Trioxide generally requires larger or complete aqueous component for dissolving, the invention has accomplished solubilization of Arsenic Trioxide in fill matrix having not more than 20%, preferably not more than 15% and most preferably not more than 10% of the aqueous component.

During development of liquid fill matrix having dissolved Arsenic Trioxide, several issues of solubility had to be resolved. A suitable solubilizing agent such as sodium hydroxide in suitable form was found essential. This suitable form was aqueous solution of sodium hydroxide which was optionally partially neutralized in the formulation. A problem of discoloration surfaced when sodium hydroxide solution came in contact with fill material polyethylene glycol. This necessitated further exploration of additional ingredients. Cosolvent and antioxidant are found useful to prevent discoloration.

In various embodiments of the present invention, a liquid fill matrices contain
 i) Arsenic Trioxide;
 ii) a solubilizing agent and optionally a neutralizing agent;
 iii) a fill material;
 iv) a co-solvent or an antioxidant or combination thereof; and
 v) optionally a surfactant, an absorption enhancer, a crystal growth inhibitor, and combinations thereof
wherein the Arsenic Trioxide is present in dissolved form in the said liquid fill matrix.

The liquid fill matrix of the present invention can be administered in number of ways such as orally, rectally, pulmonary, intravaginally, locally (ointments or drops), transdermal, parenteral administration, intravenous, intraperitoneal, intramuscular, sublingual or as a buccal or nasal spray. The most preferred way is oral, and the most preferred formulation is oral soft capsule.

Preferably, the liquid fill matrix has a neutralizing agent.

Hydrochloric acid is used as a neutralizing agent. Both sodium hydroxide and hydrochloric acid are present in the form of their aqueous solutions.

The amount of sodium hydroxide is selected from any of the following:
i) from 0.1 part to 2 parts per part of Arsenic Trioxide by weight;
ii) from 0.25 parts to 1.625 parts per part of Arsenic Trioxide by weight;
iii) from 0.4 parts to 1.375 parts per part of Arsenic Trioxide by weight;
iv) from 0.4 parts to 0.875 parts per part of Arsenic Trioxide by weight.

The present invention covers a soft capsule containing liquid fill matrix having Arsenic Trioxide in dissolved form and preferably sodium hydroxide as solubilizing agent, hydrochloric acid as neutralizing agent and fill material.

Preferably, the fill material is polyalkylene glycol.

The fill matrix may optionally contain an antioxidant. An antioxidant is selected from butylated hydroxy anisole, butylated hydroxy toluene, thioglycerol, monothioglycerol, lipoic acid, propyl gallate, methionine, cysteine, metabisulfites, sodium formaldehyde sulfoxylate, phenol-containing aromatic and aliphatic compounds and dihydrolipoic acid. Other suitable antioxidants which are soluble in polyethylene glycol can also be employed. Preferred antioxidants are butylated hydroxy anisole and butylated hydroxy toluene.

Since Arsenic Trioxide has relatively very low solubility in the polyethylene glycols, a suitable solubilizing agent is needed. Various alkalizing agents such as organic and inorganic bases are suitable for dissolving Arsenic Trioxide. Sodium hydroxide is chosen as one of the preferred solubilizing agent. The pH of the formulation of a fill matrix before encapsulation particularly in a soft gelatin capsule should not be too basic. Hence a suitable neutralizing agent is also employed in the form of acid. Hydrochloric acid in the form of its aqueous solution is preferred. The neutralizing agent causes partial neutralization to bring pH down to around 9, or in the range of 8.00 to 9.5.

Alkalizing agents are often used as solubilizing agents for Arsenic Trioxide which potentially raise pH of the composition beyond pH 12 and pH adjustment in most cases becomes necessary. Partial Neutralization process causes partial neutralization of alkalizing agents by adding acids to facilitate pH adjustment. The amount of acid employed depends on moles of alkalizing agent added. Generally, 50%-80% of the alkalizing agent added should be neutralized to achieve pH in the range of pH 8-12 for encapsulation in a soft vegan capsule or pH 8-9.5 for encapsulation in a soft gelatin capsule. In partial neutralization, moles of alkalizing agent are calculated. The acid chosen is then used in molar equivalents to cause neutralization of 50-80% of moles of alkalizing agent. For example, for neutralizing 1 mole of sodium hydroxide, 1 mole of hydrochloric acid is needed and for partial neutralization 50-80% of 1 mole of hydrochloric acid is needed. But if sodium carbonate is used as a solubilizing agent, 2 moles of hydrochloric acid are needed and 50-80% of 2 moles are needed to achieve partial neutralization. Thus, when sodium hydroxide is used as a solubilizing agent, partial neutralization is neutralization of added sodium hydroxide up to 50%, or up to 60%, or up to 70% or up to 80% by weight which means at least 50% and maximum up to 80% by weight of added sodium hydroxide is neutralized. To achieve this, moles of sodium hydroxide added are calculated and at least 50% to maximum of 80% moles of hydrochloric acid of added total moles of sodium hydroxide are employed to cause 50-80% neutralization of sodium hydroxide. If both sodium hydroxide and hydrochloric acid are used in same molar concentrations, the volume of hydrochloric acid solution required is approximately 50-80% volume of the sodium hydroxide solution to achieve partial neutralization. If sodium hydroxide and hydrochloric acid are used in different molar concentrations, the molarities should be taken into consideration while calculating the volumes or amounts. It is preferable to use the same molar concentration of sodium hydroxide and hydrochloric acid such as for example, 6M. For example, in trial 39, both solutions are 6M, the volume of hydrochloric acid required is 70% of sodium hydroxide to cause partial neutralization. In trial 36, 3M solution of Sodium hydroxide and 6M solution of hydrochloric acid are used. In this trial, the volume of sodium hydroxide is 20 ml and that of hydrochloric acid is 6.6 ml because hydrochloric acid is two times more concentrated. Hence adding 6.6 ml of 6M is similar in effect to adding 13.2 ml of 3 molar solution which is 66% volume of sodium hydroxide solution. The best method is to calculate moles of sodium hydroxide added and accordingly use 50-80% moles of hydrochloric acid. The amount of neutralizing agent needed depends on the amount needed to arrive at the desired pH range, typically greater than pH 7.91 and less than pH 13. The desired pH of the final fill matrix for encapsulation in a soft gelatin capsule is generally from pH 8-9.5 and for a vegan capsule is generally from pH 8-12.5.

Further, formulation may optionally contain one or more co-solvents. Fill matrices with and without co-solvents are successfully developed. Liquid fill matrices having lower doses of Arsenic Trioxide need lower amounts of sodium hydroxide to keep it dissolved. Such compositions may not need cosolvent for preventing discoloration.

Accordingly, the liquid fill matrix comprises
i) Arsenic Trioxide from 0.1-10% W/W; preferably from 0.1-5% W/W and more preferably from 0.1-2% W/W;
ii) sodium hydroxide as a solubilizing agent from 0.4 parts to 1.375 parts per part of Arsenic Trioxide by weight wherein sodium hydroxide is employed in form of aqueous solution from 1M to 6M; and
iii) at least 70% W/W of polyethylene glycol 400.

Cosolvent lowers pH of the solution to some extent. Such liquid fill matrix may have higher amount of hydrochloric acid in absence of a cosolvent.

Cosolvents play multiple role in the liquid fill matrix. Cosolvent helps in keeping Arsenic Trioxide in dissolved state in the liquid fill matrix. It also helps in preventing or avoiding discoloration.

Nevertheless, cosolvent is a desired ingredient of the liquid fill matrices of the present invention. Some of the preferred co-solvents which are considered include glycerin, propylene glycol, diethylene glycol, sodium lactate, various propane diols such as 2,2-propanediol, 1,1-propanediol, 1,3-propanediol. The most preferred co-solvents are glycerin and propylene glycol.

The liquid fill matrix may further comprise one or more of surfactants, absorption enhancers and crystal growth inhibitors. The liquid fill matrix is suitably encapsulated into a soft capsule.

In an embodiment, soft capsule comprises a liquid fill matrix containing
i) Arsenic Trioxide;
ii) a solubilizing agent, and a neutralizing agent;

iii) a fill material;
iv) a co-solvent or an antioxidant or combination thereof; and
v) optionally a surfactant, an absorption enhancer, a crystal growth inhibitor, and combinations thereof, wherein the liquid fill matrix comprises Arsenic Trioxide in dissolved form.

The soft capsule encapsulates liquid fill matrix as described above wherein
a) the fill material is selected from the group consisting of PEG 200, PEG 300, PEG 400, PEG 600, PEG 800 and PEG 1000, poloxamers, ethanol, dimethyl isosorbide, TRANSCUTOL™, Lauroyl Polyoxyl-32 glycerides/Lauroyl Macrogol-32 glycerides, Stearoyl polyoxyl-32 glycerides or Stearoyl macrogol-32 glycerides, Polyethylene glycol monostearate, Oleoyl macrogol-6 glycerides/Oleoyl polyoxyl-6 glycerides, Linoleoyl polyoxyl-6 glycerides NF/Linoleoyl macrogol-6 glycerides, and combinations thereof;
b) the solubilizing agent is selected from the group consisting of barium hydroxide, sodium hydroxide, potassium hydroxide, sodium metasilicate, calcium hydroxide, trisodium phosphate, potassium carbonate, sodium carbonate, ammonium hydroxide, diethylamine, triethylamine, tromethamine, picoline, dicyclohexylamine, N,N'-dibenzyl-ethylenediamine, amino acids and their salts, and combinations thereof;
c) neutralizing agent is selected from the group consisting of from sulfuric acid, carbonic acid, phosphoric acid, nitric acid, hydrochloric acid, hydrobromic acid, hydrofluoric acid, Boric acid, acetic acid, citric acid, ascorbic acid, lactic acid, acetylsalicylic acid, oxalic acid;
d) a cosolvent is selected from the group consisting of glycerin, propylene glycol, polyethylene glycol, diethylene glycol, sodium lactate, propane diol, and combinations thereof;
e) antioxidant is selected from the group consisting of butylated hydroxy anisole, butylated hydroxy toluene, thioglycerol, monothioglycerol, lipoic acid, propyl gallate, methionine, cysteine, metabisulfites, sodium formaldehyde sulfoxylate, phenol-containing aromatic and aliphatic compounds and dihydrolipoic acid and combinations thereof; and
f) the surfactant, absorption enhancer, and crystal growth inhibitor is selected from the group consisting of sodium polyacrylate, polyvinyl pyrrolidone (PVP), Macrogol 15 Hydroxystearate (SOLUTOL™), Propylene Glycol Caprylate (CAPRYOL™) Polyoxyl 40 Hydrogenated Castor Oil, and combinations thereof.

The soft capsule encapsulates a liquid fill matrix containing dissolved arsenic Trioxide wherein
a) fill material is polyethylene glycol;
b) solubilizing agent is sodium hydroxide;
c) neutralizing agent is hydrochloric acid;
d) a cosolvent is glycerin or propylene glycol; and
e) an antioxidant is butylated hydroxy toluene.

In one more embodiment of the present invention, soft capsule comprises a liquid fill matrix containing
i) Arsenic Trioxide;
ii) sodium hydroxide as a solubilizing agent, and hydrochloric acid as a neutralizing agent;
iii) polyalkylene glycol as a fill material; and
iv) an antioxidant;

wherein the liquid fill matrix comprises Arsenic Trioxide in dissolved form.

In the embodiment containing an antioxidant, it is noted that combination of i) adding neutralizing agent hydrochloric acid solution to Arsenic Trioxide solution prepared by using solubilizing agent sodium hydroxide before addition of fill material and ii) adding fill material having dissolved antioxidant obviate necessity of adding cosolvent for preventing discoloration.

In above embodiments, sodium hydroxide is employed as a solubilizing agent and hydrochloric acid as a neutralizing agent and both are employed in the form of their aqueous solutions and fill material is selected from one or more of PEG 200, PEG 300, PEG 400, PEG 600, PEG 800 and PEG 1000

The amount of sodium hydroxide is selected from any of the following:
i) from 0.1 part to 2 parts per part of Arsenic Trioxide by weight;
ii) from 0.25 parts to 1.625 parts per part of Arsenic Trioxide by weight;
iii) from 0.4 parts to 1.375 parts per part of Arsenic Trioxide by weight;
iv) from 0.4 parts to 0.875 parts per part of Arsenic Trioxide by weight.

If an embodiment contains a cosolvent, it is selected from glycerin, propylene glycol, diethylene glycol, sodium lactate, various propane diols such as 2,2-propanediol, 1,1-propanediol, 1,3-propanediol. The most preferred co-solvents are glycerin and propylene glycol. The amount of glycerin or propylene glycol or their combination is preferably not more than 20% of the total weight of the fill matrix.

If an embodiment contains an antioxidant, it is selected preferably from butylated hydroxy anisole, butylated hydroxy toluene, thioglycerol, monothioglycerol, lipoic acid, propyl gallate, methionine, cysteine, metabisulfites, sodium formaldehyde sulfoxylate, phenol-containing aromatic and aliphatic compounds and dihydrolipoic acid or any combination thereof.

A preferred embodiment according to the present invention is a soft capsule of Arsenic Trioxide as previously described having a liquid fill matrix containing both a co-solvent and an antioxidant where cosolvent is selected preferably from glycerin and propylene glycol and the antioxidant is butylated Hydroxy Toluene.

Further the embodiment does not have more than 10% of water of the total weight of the fill matrix where water comes from aqueous solutions of sodium hydroxide and hydrochloric acid.

Preferably, polyalkylene glycol is polyethylene glycol.

The soft capsule further comprises one or more of surfactants, absorption enhancers and crystal growth inhibitors.

In yet another embodiment of the present invention, soft capsule contains a liquid fill matrix having from 0.1-10%, preferably from 0.2-5% and most preferably from 0.4-2% of Arsenic Trioxide in dissolved form, from 0.1 part to 2 parts per part of Arsenic Trioxide by weight; preferably from 0.25 parts to 1.625 parts more preferably from 0.4 parts to 1.375 parts and most preferably from 0.4 parts to 0.875 parts of sodium hydroxide per part of Arsenic Trioxide, from around 0.5 parts to 0.80 parts of hydrochloric acid per part of sodium hydroxide where both sodium hydroxide and hydrochloric acid are present in the form of their aqueous solutions from 1M to 6M, at least 70% polyalkylene glycol, preferably polyethylene glycol and either a co-solvent selected from glycerin or propylene glycol or an antioxidant soluble in polyethylene glycol and wherein co-solvent is not more than 20% and preferably not more than 15% and most preferably not more than 10% and water added from aqueous solutions of sodium hydroxide and hydrochloric acid is not more than 20% and preferably not more than 15% and most preferably not more than 10%.

Some embodiments of an oral pharmaceutical formulation in the form of a soft capsule optionally comprise of one or more of surfactants, absorption enhancers and crystal growth inhibitors in addition to Arsenic Trioxide, sodium hydroxide, hydrochloric acid, polyalkylene glycol and antioxidant.

Preferred embodiments of the present invention comprise of a soft capsule having a liquid fill matrix containing
i) Arsenic Trioxide from 0.1 to 10%, preferably from 0.2-5% and most preferably from 0.4 to 2%,
ii) Sodium hydroxide preferably from 0.4 parts to 0.875 parts per part of Arsenic Trioxide in the form of an aqueous solution;
iii) hydrochloric acid in the form of an aqueous solution sufficient to achieve desired pH;
iv) at least 70% of polyethylene glycol;
v) not more than 20% of a co-solvent selected from glycerin and propylene glycol; and
vi) not more than 10% water coming from aqueous solutions of sodium hydroxide and hydrochloric acid.

The invention further provides under various embodiments various liquid fill matrices for encapsulation into a soft capsule. The liquid fill matrices have exactly the same compositions as previously described.

The invention further provides various processes to prepare liquid fill matrix of the present invention. Once the liquid fill matrix is ready, it is converted into suitable dosage form and then administered by suitable route of administration such as orally, rectally, pulmonary, intravaginally, locally (ointments or drops), transdermal, parenteral administration, intravenous, intraperitoneal, intramuscular, sublingual or as a buccal or nasal spray. The fill matrix can also be administered parenterally upon appropriate dilution with a diluent. The preferred diluent is aqueous with or without buffers and tonicity modifying agents. For aerosol administration, the fill matrix is mixed with the propellant which may include a carrier like lecithin or suitable surfactants. The most preferred route of administration is oral wherein the fill matrix is encapsulated in either a hard or soft capsules.

Various processes are employed to arrive at the desired liquid fill matrices containing Arsenic Trioxide in dissolved form and thereafter soft capsule formation.

The invention further covers a process of preparing an oral pharmaceutical formulation of Arsenic Trioxide comprising
i) preparing a liquid fill matrix containing Arsenic Trioxide in dissolved form; and
ii) encapsulating the liquid fill matrix in a soft capsule; wherein the oral formulation is a soft capsule; wherein the oral pharmaceutical formulation is a soft capsule having Arsenic Trioxide in dissolved form.

Once the liquid fill matrix is ready, encapsulation is done as per the processes known in the art. For example, a liquid fill matrix is encapsulated in a soft gelatin capsule according to processes reported in U.S. Pat. No. 5,200,191A. A person skilled in the art may adopt trivial modifications of the reported processes for better suiting the current liquid fill matrix.

Similarly, liquid fill matrix is encapsulated in a vegan soft capsule according to processes reported in U.S. Pat. No. 6,340,473B1. A person skilled in the art may adopt trivial modifications of this process for better suiting the current liquid fill matrix.

A broad general process which can encompass various specific processes that can be adopted to prepare oral pharmaceutical formulations of the present invention particularly liquid fill matrices of the present invention for encapsulation into a soft capsule is as described below.

A process of preparing liquid fill matrix for encapsulation into a soft capsule is as follows,
i) preparing from 1M to 6M solution of sodium hydroxide and from 1M to 6M solution of hydrochloric acid;
ii) solubilizing Arsenic Trioxide using sodium hydroxide to prepare a first solution;
iii) optionally adding to the first solution from 50-80% moles of hydrochloric acid of the total moles of sodium hydroxide added and mixing thoroughly to partially neutralize sodium hydroxide and to prepare a second solution;
iv) optionally adding co-solvent to (a) first solution of step ii and mixing thoroughly to prepare a second solution or b) second solution of step iii and mixing thoroughly to prepare a third solution;
v) optionally adding from 50-80% moles of hydrochloric acid solution of the total moles of sodium hydroxide added to the solution of step iv (a) and mixing thoroughly to partially neutralize sodium hydroxide and to prepare a third solution where this process step is performed in absence of step iii;
vi) optionally dissolving an antioxidant in fill material polyethylene glycol and adding polyethylene glycol solution of antioxidant to solution of step iii or solution of step iv (a) and mixing thoroughly to prepare fill matrix;
vii) optionally adding polyethylene glycol to solution of step iv (a) and mixing thoroughly to prepare fill matrix wherein this process step is performed in absence of step vi; and
viii) optionally adding one or more of surfactants, absorption enhancers, crystal growth inhibitor and mixing thoroughly to prepare liquid fill matrix;

wherein the said process involves carrying out process steps in one of the following sequences,
sequence "a": steps i, ii, iii, iv and vii; or
sequence "b": steps i, ii, iv, v and vii; or
sequence "c": steps i, ii, iii, and vi; or
sequence "d": steps i, ii, iv, v, vi;

and wherein process step viii can be combined with any sequence and wherein partial neutralization is achieved by adding from 50% to 80% moles of hydrochloric acid of the total moles of sodium hydroxide added.

Some of the preferred co-solvents which are considered include glycerin, propylene glycol, diethylene glycol, sodium lactate, various propane diols such as 2,2-propanediol, 1,1-propanediol, 1,3-propanediol. The most preferred co-solvents are glycerin and propylene glycol.

In an embodiment, sequence "b" is selected having process steps i, ii, iv, v and vii. 6 molar aqueous solutions of sodium hydroxide and hydrochloric acid are prepared. Amount of sodium hydroxide used is selected from 0.4 to 0.875 parts per part of Arsenic Trioxide. Particularly the amount is selected from 0.875, 0.7, 0.625, 0.6, 0.54, 0.5, 0.48, 0.44 and 0.4 parts of sodium hydroxide per part of Arsenic Trioxide is selected. Arsenic Trioxide is dissolved in a solution of sodium hydroxide and mixed thoroughly. Co-solvent glycerin is added in amounts from 1-10% of the total fill matrix and mixed thoroughly. Partial neutralization is done by adding from around 50-80% moles of hydrochloric acid of the total moles of sodium hydroxide added till the pH is around 9 and mixed thoroughly. Water added from aqueous solutions of sodium hydroxide and hydrochloric acid is from 1-5% of the fill matrix. Polyethylene glycol 400 or 600 is added in amounts of at least 70%, preferably in amounts of at least 80% and mixed thoroughly.

In another embodiment, sequence "c" is selected having process steps i, ii, iii, and vi. 3 molar aqueous solution of sodium hydroxide and 6 molar aqueous solution of hydrochloric acid are prepared. Amount of sodium hydroxide used is selected from 0.4 to 0.875 parts per part of Arsenic Trioxide. Particularly the amount is selected from 0.875, 0.7, 0.625, 0.6, 0.54, 0.5, 0.48, 0.44 and 0.4 parts of sodium hydroxide per part of Arsenic Trioxide. Partial neutralization is done by adding from around 50-80% moles of hydrochloric acid till the pH is around 9 and mixed thoroughly. Water added from aqueous solutions of sodium hydroxide and hydrochloric acid is from 1-5% of the fill matrix. A suitable antioxidant is chosen and used in an amount of from 0.2-2% of the weight of polyethylene glycol. Butylated hydroxy toluene is chosen in this embodiment. It is dissolved in polyethylene glycol. Polyethylene glycol 400 or 600 with dissolved antioxidants is added in amounts of at least 70%, preferably in amounts of at least 80% and mixed thoroughly to prepare the liquid fill matrix.

In two embodiments, sequence "a" is selected having process steps i, ii, iii, iv and vii. 6 molar aqueous solutions of sodium hydroxide and hydrochloric acid are prepared. In both the embodiments, the amount of sodium hydroxide used is selected from 0.4 to 0.875 parts per part of Arsenic Trioxide. Particularly the amount is selected from 0.7, 0.625, 0.5, 0.44, 0.48, 0.6, 0.54 parts of sodium hydroxide per part of Arsenic Trioxide are selected. Arsenic Trioxide is dissolved in solution of sodium hydroxide. Partial neutralization is done by adding from around 50-80% moles of hydrochloric acid of the total moles of sodium hydroxide added till the pH is around 9 and mixed thoroughly. Water added from aqueous solutions of sodium hydroxide and hydrochloric acid is from 1-5% of the fill matrix. In the first embodiment glycerin is added from 1-10% of the total fill matrix and mixed thoroughly. In the second embodiment, propylene glycol is added from 1-10% of the total fill matrix and mixed thoroughly. Polyethylene glycol is added in both the embodiments in amounts of at least 70%, preferably in amounts of at least 80% and mixed thoroughly to prepare the liquid fill matrix.

In an embodiment, sequence d is selected having steps i, ii, iv, v, vi. 6 molar aqueous solutions of sodium hydroxide and hydrochloric acid are prepared. Amount of sodium hydroxide used is selected from 0.4 to 0.875 parts per part of Arsenic Trioxide. Particularly the amount is selected from 0.875, 0.7, 0.625, 0.6, 0.54, 0.5, 0.48, 0.44 and 0.4 parts of sodium hydroxide per part of Arsenic Trioxide is selected. Arsenic Trioxide is dissolved in a solution of sodium hydroxide and mixed thoroughly. Co-solvent glycerin is added in amounts from 1-10% of the total fill matrix and mixed thoroughly. Partial neutralization is done by adding from around 50-80% moles of hydrochloric acid of the total moles of sodium hydroxide added till the pH is around 9 and mixed thoroughly. Water added from aqueous solutions of sodium hydroxide and hydrochloric acid is from 1-5% of the fill matrix. A suitable antioxidant is chosen and used in an amount of from 0.2-2% of the weight of polyethylene glycol. Butylated hydroxy toluene is chosen in this embodiment. It is dissolved in polyethylene glycol. Polyethylene glycol 400 or 600 with dissolved antioxidant is added in amounts of at least 70%, preferably in amounts of at least 80% and mixed thoroughly to prepare the liquid fill matrix.

Thus, the liquid fill matrices of the oral pharmaceutical formulations of the present invention can be prepared by adopting any one of the above sequences.

The processes to prepare liquid fill matrix having dissolved Arsenic Trioxide wherein the liquid fill matrix has from 0.1-10%, preferably 0.1-5% and most preferably from 0.1-2% of Arsenic Trioxide, from 0.1 part to 2 parts per part of Arsenic Trioxide by weight; preferably from 0.25 to 1.625 parts, more preferably from 0.4-1.375 parts and most preferably from 0.4 to 0.875 part of sodium hydroxide per part of Arsenic Trioxide, sufficient hydrochloric acid to arrive at desired pH (8-9.5 for Soft Gelatin Capsule and 8-12.5 for vegan soft capsule), at least 70% of polyalkylene glycol preferably polyethylene glycol and either a co-solvent selected from glycerin or propylene glycol or an antioxidant soluble in polyethylene glycol wherein both sodium hydroxide and hydrochloric acid are employed in the form of their aqueous solutions and wherein co-solvent is not more than 20% and preferably not more than 10% and water added from aqueous solutions of sodium hydroxide and hydrochloric acid is not more than 20% and preferably not more than 10% are carried out in 3 different ways as follows.

The first process comprises steps i, ii, iii, iv and vii; and optionally viii from general process described above and comprises,
i) preparing from 1M to 6M solution of sodium hydroxide and from 1M to 6M solution of hydrochloric acid;
ii) solubilizing Arsenic Trioxide using sodium hydroxide to prepare a first solution;
iii) adding hydrochloric acid solution to the first solution and mixing thoroughly to partially neutralize sodium hydroxide added to prepare a second solution;
iv) adding co-solvent glycerin or propylene glycol to first solution of step ii or second solution of step iii and mixing thoroughly;
vii) adding polyethylene glycol and mixing thoroughly to prepare fill; and
viii) optionally adding one or more of surfactants, absorption enhancers, crystal growth inhibitor and mixing thoroughly to prepare liquid fill matrix.

The second process comprises steps i, ii, iv, v and optionally viii from general process described above and comprises
i) preparing from 1M to 6M solution of sodium hydroxide and from 1M to 6M solution of hydrochloric acid;
ii) solubilizing Arsenic Trioxide using sodium hydroxide to prepare a first solution;
iv) adding co-solvent glycerin or propylene glycol to first solution of step ii or second solution of step iii and mixing thoroughly;
v) adding hydrochloric acid solution to the first solution and mixing thoroughly to partially neutralize sodium hydroxide added to prepare a second solution where this process step is performed in absence of step iii;
vii) adding polyethylene glycol and mixing thoroughly to prepare fill matrix; and
viii) optionally adding one or more of surfactants, absorption enhancers, crystal growth inhibitor and mixing thoroughly to prepare liquid fill matrix.

The third process comprises steps i, ii, iii, vi and optionally viii from general process described above and comprises
i) preparing from 1M to 6M solution of sodium hydroxide and from 1M to 6M solution of hydrochloric acid;
ii) solubilizing Arsenic Trioxide using sodium hydroxide to prepare a first solution;

iii) adding hydrochloric acid solution to the first solution and mixing thoroughly to partially neutralize sodium hydroxide added to prepare a second solution;

vi) dissolving an antioxidant in fill material polyethylene glycol and adding polyethylene glycol solution of antioxidant to solution of step iii and mixing thoroughly to prepare fill matrix; and viii) optionally adding one or more of surfactants, absorption enhancers, crystal growth inhibitor and mixing thoroughly to prepare liquid fill matrix.

Further, a fourth process can be selected incorporating both cosolvent and antioxidant and the process steps are according to the sequence "d".

The pharmaceutical formulations of the present invention are used for treating cancer or abnormal cell proliferation condition selected from Acute lymphoblastic leukemia (ALL), Acute lymphoblastic B-cell leukemia, Acute lymphoblastic T-cell leukemia, Acute myeloblastic leukemia (AML), Acute promyelocytic leukemia (APL), Acute monoblastic leukemia, Acute erythroleukemic leukemia, Acute megakaryoblastic leukemia, Acute myelomonocytic leukemia, Acute undifferentiated leukemia, Chronic myelocytic leukemia (CML), Chronic lymphocytic leukemia (CLL), hairy cell leukemia, polycythemia Vera, Hodgkin's lymphoma, non-Hodgkin's lymphomas, myeloma, giant cell myeloma, indolent myeloma, localized myeloma, multiple myeloma, plasma cell myeloma, Sclerosing myeloma, Solitary myeloma, Smoldering multiple myeloma, non-secretary myeloma, osteosclerotic myeloma, plasma cell leukemia, Solitary plasmacytoma, extramedullary plasmacytoma, high grade lymphoma, intermediate grade lymphoma, low grade lymphoma, lung cancer, Hepatocellular Carcinoma, Myelodysplastic Syndromes, P53 Mutation, Brain and Central Nervous System Tumors, Extragonadal Germ Cell Tumor, Multiple Myeloma and Plasma Cell Neoplasm, Acute Promyelocytic Leukemia with PML-RARA, Unspecified Adult Solid Tumor, Protocol Specific Lymphoma, Myelodysplastic/Myeloproliferative Neoplasms, AML, Stage II Multiple Myeloma, Stage III Multiple Myeloma, Refractory Plasma Cell Neoplasm, Relapsed Acute Promyelocytic Leukemia, Childhood Acute Promyelocytic Leukemia (M3), Refractory Cancer, Intractable Cancer, NPMc+ AML, Neuroblastoma, Ovarian Cancer, Endometrial Cancer, Endometrial Carcinoma, Non-small Cell Lung Cancer, Adult Acute Megakaryoblastic Leukemia (M7), Adult Acute Minimally Differentiated Myeloid Leukemia (M0), Adult Acute Monoblastic Leukemia (M5a), Cancer of Lung, Pulmonary Cancer, Skin Basal Cell Carcinoma, Metastatic Melanoma, Chronic Myelogenous Leukemia, Leukemia, Lymphocytic, Chronic, B-Cell, Stem Cell Transplantation, Cancer Other Than Leukemia, Recurrent Transitional Cell Cancer of the Renal Pelvis and Ureter, Recurrent Urethral Cancer, Transitional Cell Carcinoma of the Bladder, Ureter Cancer, Extranodal Marginal Zone B-cell Lymphoma of Mucosa-associated Lymphoid Tissue, Nodal Marginal Zone B-cell Lymphoma, Prolymphocytic Leukemia, Adenocarcinoma of the Esophagus, Stage III Esophageal Cancer, Stage IV Esophageal Cancer, Primary Hepatocellular Carcinoma, Acute Myelogenous Leukemia, Childhood Germ Cell Tumor, Essential Thrombocythemia, Primary Myelofibrosis, Refractory Multiple Myeloma, Adult Giant Cell Glioblastoma, Adult Glioblastoma, Adult Gliosarcoma, Pancreatic Cancer, Chronic Lymphocytic Leukemia, Small Lymphocytic Lymphoma, Liver Cancer, Unspecified Childhood Solid Tumor, Protocol Specific, Breast Cancer, Myelodysplastic Syndrome (MDS), Kidney Cancer, Testicular Germ Cell Tumor, Cervical Cancer, Prostate Cancer, Leukemia, Promyelocytic, Acute, Myeloid Malignancy MDS, Brain Cancer, Chronic Myeloproliferative Disorders, Relapsed/Refractory Acute Myeloid Leukemia, Myelofibrosis, Colorectal Cancer, Stage I Multiple Myeloma, Refractory Acute Promyelocytic Leukemia, Adult Acute Myeloid Leukemia With t(15; 17)(q22; q12), Adult Acute Promyelocytic Leukemia (M3), Advanced Hematological Disorders, Untreated Childhood Acute Myeloid Leukemia and Other Myeloid Malignancies, Chronic Myelomonocytic Leukemia, Promyelocytic Leukemia, Acute Torsades de Pointe Caused by Drug Long QT Syndrome, CD33 Positive Acute Myelogenous Leukemia, Urothelial Carcinoma, Bladder Cancer, Urinary Bladder Neoplasms, Childhood Acute Promyelocytic Leukemia, Recurrent Acute Leukemia of Ambiguous Lineage, Recurrent Acute Lymphoblastic Leukemia, Recurrent Acute Myeloid Leukemia.

Particularly, the formulations of the present invention are employed in treating cancer or condition mediated by abnormal cell proliferation in a patient in need thereof wherein cancer or abnormal cell proliferation condition is preferably selected from Acute promyelocytic leukemia (APL), Myelodysplastic Syndromes, Acute myeloblastic leukemia (AML) and Multiple Myeloma. They are also employed in treating chronic Graft versus Host Disease in a patient in need thereof.

The method of treating cancer or condition mediated by abnormal cell proliferation or the method of treating chronic Graft versus Host Disease comprises administering to a patient suffering from such disease a pharmaceutical formulation particularly a soft capsule which can deliver a unit dose of Arsenic Trioxide from 0.1 mg to 25 mg, preferably from 1 mg-25 mg and most preferably from 1 mg-20 mg. Preferably, a daily dose from 1-20 mg should be administered.

No art till date provides a liquid fill matrix containing dissolved Arsenic Trioxide suitable for converting into various dosage forms wherein such liquid fill matrix has not more than 20% of the aqueous component and not less than 80% of the nonaqueous component. In particular, no art till date provides soft capsules of Arsenic Trioxide containing dissolved Arsenic Trioxide. Arriving at soft capsule formulation of Arsenic Trioxide comprising a liquid fill matrix having Arsenic Trioxide in dissolved form was extremely challenging. Owing to poor solubility, hazardous nature and stringent exposure limits on Arsenic Trioxide, manufacturing suitable safer oral dosage forms is particularly difficult. Further, the formulation should be such that Arsenic Trioxide remains in dissolved form after ingestion and stays in dissolved form in gastrointestinal fluids from where it gets completely absorbed. This necessitates that once dissolved Arsenic Trioxide should remain in solution in spite of getting diluted with liquids having low solubility.

As reported in various prior arts,
i) Arsenic Trioxide powder is sparingly and extremely slowly soluble in cold water; even in boiling water it is only soluble in a 1:15 ratio;
ii) Arsenic Trioxide is insoluble in alcohol, chloroform, and ether;
iii) the solubility of Arsenic Trioxide in 100 g of water is 1.2 g at 0° C., 2.1 g at 25° C., and 5.6 g at 75° C. The rate of dissolution is very low, and several weeks are required to achieve equilibrium;
iv) Ethanol, isopropyl alcohol, SLS, Tweens, cyclodextrin, poloxamer etc. could not dissolve Arsenic Trioxide;

Hence, it is noted that most commonly used solubilizing agents do not solubilize Arsenic Trioxide.

First constraint is solubilizing Arsenic Trioxide. Achieving the necessary and meaningful solubility of Arsenic Trioxide in the fill matrix from which it is fully released and well absorbed and wherein such fill matrix is suitable for encapsulation in a soft capsule is tricky.

Apart from solubility in the fill matrix, a soft capsule cannot encapsulate any solution which is predominantly aqueous. All prior art solutions reported for Arsenic Trioxide are aqueous solutions and cannot be incorporated in a soft capsule.

Second constraint is the restricted volume of aqueous component in a soft capsule. Majority of the contents of a soft capsule such as fill materials, solvents and cosolvents are nonaqueous. For example, most popular fill materials such as polyalkylene glycols are non-aqueous although hydrophilic. The aqueous component should be restricted to not more than 20% and preferably not more than 10% of the fill matrix. Hence the volume available to dissolve Arsenic Trioxide in a fill matrix is very small.

Volume of aqueous component is also restricted due to composition of the shell of the capsule. A typical soft gelatin capsule shell composition is composed of gelatin, glycerin, sorbitol and, may contain antimicrobial agents along with coloring and opacifying agents. As reported by Gullapalli Rampurna Prasad (2010), the reported water contents of the fill and the shell at equilibrium were 6.4±0.1% and 9.6±0.2%, respectively for the PEG 400 based fill. It is not only desirable to restrict water content of the fill matrix to not more than 20%, preferably not more than 15% and most preferably not more than 10% but it is more desirable to restrict water content of fill matrix to around water content of the capsule shell.

Fill matrix in the soft capsule should be predominantly non-aqueous. Therefore ideally at least 80% of the fill matrix should be non-aqueous. In a soft capsule of size around 0.5 cc-1 cc, if at least 80% of the fill matrix should be non-aqueous, the volume available for aqueous components is restricted to only a few hundred microliters.

Various prior arts provide aqueous solutions of Arsenic Trioxide such as 1 mg/ml to 33 mg/ml. For 1 mg/ml solution, to deliver a dose of 10 mg or 20 mg, one needs to take 10 ml or 20 ml of the aqueous solution. Such a volume is exceptionally large which cannot be encapsulated in any capsule. Also, predominantly aqueous solutions cannot be encapsulated.

Another prior art discussed under background section discloses a lyophilized formulation of Arsenic Trioxide. An exemplary formulation is provided therein in which an aqueous Arsenic Trioxide solution is prepared at a concentration of 33 mg/ml. This solution will need to be substantially diluted with the non-aqueous fill material such that the fill matrix has a final aqueous component of 10% or less. There is a potential apprehension of precipitation after such dilution by a non-aqueous component.

Also, a much more concentrated aqueous solution of Arsenic Trioxide than 33 mg/ml is desired to achieve a final dose of 25 mg or 20 mg or even 10 mg in a liquid fill matrix having only 10% of such aqueous component. The present invention has achieved in trial 37, a 170.21 mg/ml aqueous solution of Arsenic Trioxide in solution of sodium hydroxide which is partially neutralized. The invention has also achieved in trial 41, a 540 mg/ml aqueous solution of Arsenic Trioxide in solution of sodium hydroxide. The present invention recommends preparation of around 200 mg/ml and preferably around 300 mg/ml concentrated aqueous solution of Arsenic Trioxide which upon dilution by a nonaqueous component can form a liquid fill matrix which does not show any precipitation where such liquid fill matrix contains only up to 10% of such aqueous solution and is predominantly nonaqueous and there is no precipitation of Arsenic Trioxide when the aqueous solution comprising Arsenic Trioxide is diluted with a nonaqueous component.

The inventor in the present invention pondered upon and unravels issues of solubilization of Arsenic Trioxide and accommodating aqueous component having dissolved Arsenic Trioxide in soft capsule having predominantly nonaqueous hydrophilic matrix.

Since Arsenic Trioxide is sparingly and extremely slowly soluble in water and relatively insoluble in nonaqueous material such as polyethylene glycol, therefore, the real challenge was to solubilize Arsenic Trioxide in the fill matrix having at least 80% of non-aqueous components including fill material such as polyethylene glycol.

Many trials some of which are presented below finally led to successful development of a soft capsule fill matrix having not more than 20% and preferably not more than 10% of aqueous component and at least 80% nonaqueous component yet such fill matrix could keep Arsenic Trioxide in dissolved form. These formulations in the form of a soft capsule can deliver a unit dose of Arsenic Trioxide from 0.1 mg to 25 mg, preferably from 1 mg-25 mg and most preferably from 1 mg-20 mg.

All experiments are designed to arrive at suitable liquid fill matrices which can be converted into final oral pharmaceutical formulation of Arsenic Trioxide containing Arsenic Trioxide in dissolved form, preferably a soft capsule of Arsenic Trioxide containing Arsenic Trioxide in dissolved form.

First set of experiments is carried out to determine the solubilizing agent and its amount. Preferred solubilizing agent was the alkalizing agent.

Arsenic Trioxide can be dissolved using a solubilizing agent such as an alkalizing agent. An alkalizing agent can be one or more selected from barium hydroxide, sodium hydroxide, potassium hydroxide, sodium metasilicate, calcium hydroxide, trisodium phosphate, potassium carbonate, sodium carbonate, ammonium hydroxide, diethylamine, triethylamine, tromethamine, picoline, dicyclohexylamine, N,N'-dibenzyl-ethylenediamine, and amino acids including arginine, lysine and glycine, and their salts. Preferred alkalizing agents are potassium hydroxide and sodium hydroxide.

Amongst alkalizing agents, sodium hydroxide is chosen as it has been reported in various arts as the most preferred solubilizing agent for Arsenic Trioxide. Sodium hydroxide is employed in the form of its aqueous solution. Different molar solutions of sodium hydroxide were tried from 0.125M to 6M. Solutions from 1M to 6 M are preferred. Solutions from 3M-6M are most preferred. Water contributed to the fill matrix, through sodium hydroxide solutions of different molarities, also exhibited some impact on solubility of Arsenic Trioxide. Along with the solubilizing agents, necessity for incorporating one or more co-solvents was also considered for dissolution of Arsenic Trioxide. Some of the preferred co-solvents which are considered include glycerin, propylene glycol, diethylene glycol, sodium lactate, various propane diols such as 2,2-propanediol, 1,1-propanediol, 1,3-propanediol. The most preferred co-solvents are glycerin and propylene glycol.

Second set of experiments is carried out to optimize fill matrix composition. A third set of experiments is carried out to optimize the process of preparing suitable oral pharmaceutical formulations of Arsenic Trioxide containing Arsenic Trioxide in dissolved form.

While developing a suitable product and process, surprisingly, discoloration surfaced upon mixing of solubilizing agent viz. sodium hydroxide solution with fill material. viz. polyethylene glycol. In various embodiments of example 2 (trials 11-20), when around 13 ml (around 14.69 mg)-14.7 ml (around 16.6 mg) polyethylene glycol is pretreated with 100 mg-650 mg of sodium hydroxide, discoloration was observed. The discoloration was particularly observed when the sodium hydroxide content in PEG was sufficiently high (>5 mg/ml) to accommodate the solubilization of Arsenic Trioxide at appropriate concentration to deliver the therapeutic dose (10-20 mg).

FIG. 1 provides discoloration that occurred when polyethylene glycol was pretreated with various molar concentrations of sodium hydroxide where the sodium hydroxide content in PEG was sufficiently high such as >5 mg/ml. It is observed that the discoloration intensified with higher amounts of sodium hydroxide. More the amount of sodium hydroxide required to dissolve Arsenic Trioxide, more distinct was the discoloration. This also meant that one can probably control discoloration by using lesser amounts of sodium hydroxide. But such a lesser amount will not dissolve Arsenic Trioxide in sufficient amounts to deliver doses such as 10 mg and 20 mg. However, if one desires to prepare dosage forms of significantly lower strength; then the corresponding sodium hydroxide content in PEG would be reduced obviating any issues with color formation. Thus, in a three-component system having Arsenic Trioxide, Sodium hydroxide in the form of its aqueous solution and polyethylene glycol, discoloration emerged as a major limitation in developing liquid fill matrix. Discoloration emerged as a third constraint in further development till a suitable solution for discoloration was sought. This further led to a fourth set of experiments to resolve discoloration.

These sets of experiments are not necessarily isolated experiments or experiments carried out sequentially. For example, some experiments were intended to simultaneously resolve issues of solubility, discoloration and process optimization etc.

Experiments were conducted 1. to find out amount of sodium hydroxide required to solubilize Arsenic Trioxide (example 1, trials 1-10);

2. to find out Solubility of Arsenic Trioxide in mixture of aqueous and non-aqueous components which is representative of a fill matrix. If Arsenic Trioxide is dissolved in sodium hydroxide solution and then added to a nonaqueous component, chances of precipitation are quite high. To avoid this, Arsenic Trioxide is added into polyethylene glycol pretreated with sodium hydroxide which can resemble a fill matrix. (Example 2, trials 11-20);

However, several surprising effects are observed from above two experiments (example 1 and 2) Amphoteric nature of Arsenic Trioxide produced reduction in pH as it got dissolved in sodium hydroxide solution. Even when a sufficient amount of sodium hydroxide is present, addition of more and more Arsenic Trioxide would considerably reduce pH and finally precipitate out.

In trials under example 2, discoloration surfaced when pretreatment of polyethylene glycol is done with sodium hydroxide. This was an unforeseen challenge. One more challenge emerged was that the amount of solubilizing agent required to solubilize the same amount of Arsenic Trioxide suddenly increased in presence of polyethylene glycol.

With these early obstacles, further trials focused on improving solubilization of Arsenic Trioxide and finding solution for discoloration and include trials:

3. to improve the solubilization ratio of sodium hydroxide to Arsenic Trioxide in polyethylene glycol pretreated with sodium hydroxide by varying water content; (trials 21-24)

4. to avoid discoloration of polyethylene glycol when pretreated with sodium hydroxide by adding an antioxidant in polyethylene glycol before its pretreatment with sodium hydroxide; (trials 25-26);

5. to explore role of co-solvent and evaluate glycerin as a co-solvent; (trials 27-28)

6. to change order of mixing and to avoid pretreatment of glycerin with sodium hydroxide where glycerin is added after dissolving Arsenic Trioxide in sodium hydroxide solution; (trials 29-31);

7. to employ a combination of glycerin and polyethylene glycol where neither is pretreated with sodium hydroxide and order of mixing is kept as preparing solution of Arsenic Trioxide, adding glycerin and subsequently adding polyethylene glycol and checking for discoloration if any. (trials 32-35);

8. to prepare concentrated solution of Arsenic Trioxide having concentration of 200 mg/ml, substantially higher than earlier 20 mg/ml, and to observe effect of pH adjustment (trial 36);

9. Preparation of fill matrix from pH adjusted Concentrated Arsenic Trioxide solution providing two options viz. an option with co-solvent and without co-solvent (trials 37-38A and 38B);

10. to arrive at the best products and process for preparing final fill matrices by changing order of addition of ingredients (trials 39-42).

Trials are briefly summarized below and provided in detail under the example section.

Trials 1-10

Example 1 provides various experiments done under trials 1-10 to determine the minimum amount of sodium hydroxide required to dissolve Arsenic Trioxide. Trials involve dissolving 400 mg of Arsenic Trioxide using varying amounts of sodium hydroxide in increments of 50 mg from 100 mg to 650 mg in 20 ml water. All trials successfully produced an aqueous solution of Arsenic Trioxide of 20 mg/ml (400 mg in 20 ml).

There were two critical observations from the above experiment. First, the 0.25 parts of Sodium hydroxide was able to dissolve 1 part of Arsenic Trioxide. Addition of Arsenic Trioxide to the sodium hydroxide solution leads to the dramatic decrease in pH from 13.94 to 9.4. Arsenic Trioxide is an amphoteric oxide, which upon addition to water, decreases the pH of a solution when solubilized. This drop in pH would continue if more Arsenic Trioxide is added to the same solution ultimately resulting in precipitation. The second observation is that this dramatic drop in pH can be prevented by using higher amounts of sodium hydroxide in the same volume of solvent. As mentioned in Trial 10, the drop in pH is from 14.35 to only 13.63. Thus, higher the molarity of the sodium hydroxide solution, more concentrated solutions of Arsenic Trioxide could be prepared.

The liquid fill matrix of the present invention is developed for preparing various further dosage forms, particularly and preferably for developing a soft capsule form. A soft capsule contains a fill matrix comprising predominantly a fill material which is non-aqueous. Polyethylene glycol of different grades or their combinations are preferably employed as fill materials. Since example 1 could produce aqueous solutions of Arsenic Trioxide, further attempt was made to achieve this concentration in a mixture of aqueous and nonaqueous components which can be representative of a fill matrix.

Arsenic Trioxide has very low solubility in polyethylene glycol. Hence, polyethylene glycol cannot serve as a vehicle to dissolve Arsenic Trioxide in sufficient quantity to deliver the needed therapeutic dose. Since, Arsenic Trioxide has low solubility in polyethylene glycol; there exists a potential possibility of precipitation of Arsenic Trioxide from its dissolved form from sodium hydroxide solution of Example 1 upon mixing with PEG. Hence, this constraint was addressed in the trials 11-20 by pretreating PEG with sodium hydroxide and then adding Arsenic Trioxide to it.

Trials 11-20

Example 2 provides various experiments done under trials 11-20 where solubility of Arsenic Trioxide was evaluated in polyethylene glycol pretreated with sodium hydroxide. Out of the total amount of polyethylene glycol, 75% (13 ml to 14.7 ml) is pretreated with varying amounts of sodium hydroxide (from 100-650 mg in increments of 50 mg) in the form of 6M aqueous solution. Arsenic Trioxide 400 mg and remaining 25% of polyethylene glycol are added for achieving 20 mg/ml solution of Arsenic Trioxide. Only higher amounts of sodium hydroxide from 550 mg-650 mg could dissolve 400 mg of Arsenic Trioxide. The ratio of Sodium hydroxide to Arsenic Trioxide is 1.375:1 (for 550 mg of sodium hydroxide) and 1.625:1 for 650 mg of Arsenic Trioxide. Discoloration was produced immediately after pretreatment and before adding Arsenic Trioxide. FIG. 1 shows discoloration of polyethylene glycol upon pretreatment with different amounts of sodium hydroxide.

The minimum ratio of Sodium hydroxide to Arsenic Trioxide to dissolve Arsenic Trioxide is now changed from its previous ratio of 1:4 (achieved in example 1) to 1:0.73 in presence of polyethylene glycol. Earlier 1 part of sodium hydroxide could dissolve 4 parts of Arsenic Trioxide (0.25 parts of sodium hydroxide could dissolve 1 part of Arsenic Trioxide). However, in the presence of polyethylene glycol, 1 part of sodium hydroxide could dissolve only 0.73 parts of Arsenic Trioxide.

Several further trials were simultaneously taken to enhance solubility and to avoid discoloration.

Trials 21-24

Role of the amount of water coming from aqueous solution of sodium hydroxide was thought crucial in further enhancing solubilization of Arsenic Trioxide. Trials 21-24 of example 3 respectively employed 3 molar solution of sodium hydroxide delivering from 100 mg-250 mg sodium hydroxide thus employing increasing volume of sodium hydroxide solution. Out of the total amount of PEG 400, 75% of the quantity was taken and pretreated with 3 M sodium hydroxide to deliver 100 mg-250 mg of sodium hydroxide. This was followed by addition of 400 mg of Arsenic Trioxide and finally adding remaining 25% polyethylene glycol. The water content, contributed by 3M sodium hydroxide solution, for trials 21-24 were 4.15, 6.25, 8.35 and 10.4% respectively.

In trials 21-23 Arsenic Trioxide did not dissolve completely. It has been surprisingly noted that in trial 24 which provided complete dissolution of Arsenic Trioxide, the solubilization ratio of Sodium hydroxide to Arsenic Trioxide was improved from 1:0.73 (example 2) to 1:1.6. This was possible by increasing the water content to 10.4% of the final solution. The key learning from this experiment was that the solubility of Arsenic Trioxide in the pretreated PEG can be manipulated by changing the molarity of the sodium hydroxide solution. However, in a soft capsule, usually water content is kept as low as possible and most preferably not more than 10%. Hence, further experimentation was needed to enhance solubility of Arsenic Trioxide with low water content of fill matrix.

Trials 25-26—Trials Using Antioxidant

All trials 21-24 exhibited discoloration and this discoloration was independent of Arsenic Trioxide. To prevent discoloration, trials with an antioxidant butylated hydroxy toluene (BHT) were conducted. Example 4 presents data from trials 25 and 26 where two different concentrations of BHT viz. 0.2% and 2% were added to polyethylene glycol and stirred to dissolve completely. This was followed by adding 550 mg of sodium hydroxide. Clear yellowish, orange-colored solutions were instantly formed upon addition of sodium hydroxide. BHT could not completely prevent discoloration of polyethylene glycol, but the intensity of the color was dramatically reduced. Hence, one could potentially employ an antioxidant such as BHT in the final fill matrix to prevent color formation upon long term storage.

Trials Using Co-Solvents

Further, the role of co-solvent is explored to reduce the amount of solubilizing agent. Less is the solubilizing agent, less will be the discoloration. It was desired to identify a co-solvent which would withstand the discoloration at high pH and enhance the solubility of Arsenic Trioxide.

Some of the co-solvents which are considered include glycerin, propylene glycol, diethylene glycol, sodium lactate, various propane diols such as 2,2-propanediol, 1,1-propanediol, 1,3-propanediol. The co-solvents glycerin and propylene glycol are selected for trials. Solubility of Arsenic Trioxide is reported in glycerin. Glycerin is also compatible with polyalkylene glycols.

Hence, few inhouse trials (not illustrated here) are taken where dissolving Arsenic Trioxide in glycerin pretreated with sodium hydroxide is attempted. In five different vials, 75% of the total amount of glycerin is taken and pretreated with 6M solution of sodium hydroxide (volume added is from 0.42 ml-2.2 ml). After mixing thoroughly, Arsenic Trioxide and remaining 25% of glycerin are added and mixed thoroughly.

It was observed that Arsenic Trioxide is not only dissolved in glycerin pretreated with the hydroxides successfully, but even the amount of sodium hydroxide needed was much lower compared to the amount needed for pretreating PEG 400 for dissolving Arsenic Trioxide. This suggests that solubility of Arsenic Trioxide in glycerin pretreated with sodium hydroxide is better than its solubility in polyethylene glycol pretreated with sodium hydroxide. The minimum ratio of Sodium hydroxide to Arsenic Trioxide to dissolve is now changed to 1:1.33 from 1:0.73 observed with PEG 400 under similar conditions. Thus, a minimum of 300 mg of NaOH is needed to dissolve 400 mg of ATO. Here the ratio of sodium hydroxide to Arsenic Trioxide is 1:1.33 or 0.75:1. This data suggests that Glycerin could potentially act as a cosolvent in the fill matrix for soft gelatin capsules.

Further, surprisingly it was noted that pretreatment of glycerin with sodium hydroxide did not cause any discoloration reaction which was observed while pretreatment of polyethylene glycol with sodium hydroxide. However, glycerin can neither replace fill material nor can be added in remarkably high amounts in fill matrix and hence, enhancing solubility of Arsenic Trioxide in fill matrix predominantly containing fill material polyethylene glycol was essential. It was also essential to investigate the impact of glycerin on the color formation in the fill matrix.

Trials 27-28

Example 5 provides experiments done under trials 27 and 28 to study impact of co-solvent on discoloration. Trials 27 and trial 28 of example 5 respectively employed 3 M solution of sodium hydroxide to deliver 250 mg of sodium hydroxide in a vial to treat polyethylene glycol in trial 27 and glycerin in trial 28. A total water content for each trial was 10.4%. Arsenic Trioxide 400 mg was added to each vial and stirred. Trial 27 provided a clear but colored solution. In trial 28, it was again noted that replacing PEG with Glycerin completely prevented discoloration. Although the solution was somewhat turbid in the beginning, on standing the turbidity disappeared and a clear colorless solution was observed.

Thus, a three-component system of sodium hydroxide solution, polyethylene glycol and Arsenic Trioxide provides a clear but colored solution while a three-component system of sodium hydroxide solution, glycerin and Arsenic Trioxide provides a colorless solution.

In all of the above trials, PEG or Glycerin was first pretreated with sodium hydroxide and Arsenic Trioxide was added to the pretreated solution. During the experimentation with Glycerin; it was serendipitously discovered that if Arsenic Trioxide is dissolved first in sodium hydroxide solution, and then that solution is added to Glycerin; a highly concentrated solution of Arsenic Trioxide (157.4 mg/ml) could be formed in presence of Glycerin; where the Arsenic Trioxide stays in solution and no color formation occurs. This discovery was important as it emphasized the importance of order of addition of ingredients.

Trials 29-31

Trials 29-31 of example 6 are conducted to check the effect of order of mixing with glycerin. First, a 3 molar (3M) solution of sodium hydroxide was prepared and added in three separate vials respectively delivering 250, 300 and 350 mg of sodium hydroxide. Arsenic Trioxide 400 mg was added in each vial and stirred for around 15-30 minutes. All vials showed a clear solution. The ratio of sodium hydroxide to Arsenic Trioxide are 0.625:1 (for 250 mg of sodium hydroxide for 400 mg of Arsenic Trioxide), 0.75:1 (for 300 mg of sodium hydroxide for 400 mg of Arsenic Trioxide) and 0.875:1 (for 350 mg of sodium hydroxide for 400 mg of Arsenic Trioxide). The corresponding concentrations of Arsenic Trioxide in trials 29-31 are around 192 mg/ml, 160 mg/ml and 137 mg/ml respectively. For the first time, such concentrated solutions of Arsenic Trioxide were prepared. No art has ever reported around 200 mg/ml solution of Arsenic Trioxide. Subsequently, glycerin was added. All vials produced clear solutions and no discoloration was observed. The lowest ratio of sodium hydroxide to Arsenic Trioxide in these trials where Arsenic Trioxide is successfully dissolved is changed to 0.625:1.

The difference between trials 28 and 29 is the order of adding Glycerin. While trial 28 included pretreating glycerin with sodium hydroxide before adding Arsenic Trioxide, trial 29 included adding glycerin in already dissolved Arsenic Trioxide solution.

These trials viz. trials 29-31 emphasized on order of mixing ingredients. If glycerin is pretreated with sodium hydroxide, it reduces the dissolution rate of Arsenic Trioxide. Thus, it is preferable if a solution of Arsenic Trioxide is first prepared in sodium hydroxide solution and then mixed with glycerin. In this process, neither discoloration nor turbidity is observed and capacity of Glycerin to act as a co-solvent is restored. The same order of mixing is found essential for propylene glycol.

All earlier trials involving pretreatment of polyethylene glycol with sodium hydroxide had produced discoloration. However, no trial containing glycerin and excluding polyethylene glycol exhibited discoloration. Since soft capsules can't incorporate very high amounts of glycerin and since polyethylene glycol is the most essential and major ingredient of the fill matrix, trials containing combinations of glycerin and polyethylene glycol were considered. A quaternary system containing Arsenic Trioxide, sodium hydroxide, glycerin and polyethylene glycol was thus planned. The order of addition of ingredients was selected from example 6 which does not involve pretreatment of any ingredient with sodium hydroxide. Arsenic Trioxide solution in sodium hydroxide was prepared and other ingredients were subsequently mixed. First glycerin is mixed with Arsenic Trioxide solution and subsequently, polyethylene glycol was added and mixed thoroughly.

Trials 32-35

Example 7 represents trials 32-35 where no pretreatment is done and order of adding ingredients is changed to first preparing a concentrated solution of Arsenic Trioxide (200 mg/ml) and then adding glycerin and finally polyethylene glycol.

Trials 32-35 were also designed to incorporate increasing amounts of glycerin viz. 1.8 ml or 1 part, 5.4 ml or 3 parts, 9 ml or 5 parts and 12.6 ml or 7 parts and decreasing amounts of polyethylene glycol viz. 16.2 or 9 parts, 12.6 ml or 7 parts, 9 ml or 5 parts, 5.4 ml or 3 parts. Amounts of Arsenic Trioxide and sodium hydroxide are constant in trials 32-35.

The trials 32 and 33 produced yellow-colored solutions. Intensity of yellow color was less in trial 33 having more glycerin than trial 32. The samples of Trial 34 and 35 were colorless initially but developed a very mild yellow color upon storage. There were two distinct and key observations from these trials. First, that increasing the glycerin content dramatically reduces the color formation, and second, that reducing the PEG content of the formulation also helps in reducing the color formation. Without bound by the mechanism on how glycerin has an effect on color formation; it is postulated that the addition of mildly acidic glycerin might be lowering the pH of the solution and thus preventing the color formation.

As an alternative to glycerin, another co-solvent propylene glycol was also tried in other trials because it is compatible with the fill material (PEG) and is mildly acidic in water. The results with propylene glycol were exactly similar to that of Glycerin suggesting that the pH of the Arsenic Trioxide solution plays some role in the color formation.

Role of pH was found interesting because solutions with higher pH having higher amounts of sodium hydroxide readily dissolve Arsenic Trioxide, but higher pH solutions also produce discoloration. As pH is lowered, one may get rid of discoloration but there is an apprehension of precipitation of Arsenic Trioxide.

Further trials were planned to investigate role of pH in obtaining clear and colorless solution of Arsenic Trioxide, Trial 36

The role of pH was investigated in this trial by first determining the lower limit of pH where Arsenic Trioxide starts precipitating out of the sodium hydroxide solution. In Trial 36, a concentrated solution of Arsenic Trioxide (200 mg/ml) was first prepared and then partially neutralized by 6 M HCl. It was observed that the concentrated Arsenic Trioxide solution stayed clear up to pH 9.58, then it started becoming hazy when pH reached to 8.5. At pH 7.91 Arsenic Trioxide started precipitating out. This also suggested that suitable pH of Arsenic Trioxide should always be higher than 7.91 or at least 8.

Trials 37-38A and 38B

In Trials 37 and 38A, the effect of adjusting pH and glycerin on the clarity of the solution was investigated. First a stock solution of Arsenic Trioxide in sodium hydroxide (200 mg/ml) using 3M NaOH is prepared. To one of the stock solutions 3.5 ml of 6M HCl was added and to another 5.5 ml of 6M HCl was added respectively. The resulting pHs after partial neutralization were 10.04 and 9.07, respectively. These two partially neutralized solutions were further treated as described under part 1 and part 2.

Part 1: In the first part, 2 ml of each partially neutralized solution was mixed with 18 ml of PEG 400.

When 2 ml of pH 10.04 solution is mixed with 18 ml of PEG 400, a slightly yellow colored but hazy solution. is produced.

When 2 ml of pH 9.07 solution is mixed with 18 ml of PEG 400, a clear and colorless solution is produced suggesting that the lower pH of the concentrated Arsenic Trioxide solution prevents the color formation in PEG and still provides a clear solution which is suitable for encapsulation. The pH 9.07 solution, after adding polyethylene glycol, gets diluted to provide a 20 mg/ml solution of Arsenic Trioxide having around 90% fill material (18 ml). This formulation has all desired attributes such as pH, around 90% fill material and water content around 10%. This solution can be directly encapsulated.

This trial is very important as it led to another discovery that, clear and colorless fill matrix can be developed without a co-solvent. Trial 38A part 1 treatment demonstrated that a clear fill matrix solution of Arsenic Trioxide could be prepared without the use of glycerin. However, this clear solution can develop a slight yellowish tint upon storage. Based on the learnings for Trials 25 and 26; it is possible to eliminate this slight yellow tint by including an antioxidant in the solution. Suitable antioxidants are butylated hydroxy anisole, butylated hydroxy toluene and certain thiol antioxidants which are soluble in polyethylene glycol. The inventor proposes an exemplary trial incorporating an antioxidant in part 1 treatment of trial 38A. This trial is provided as trial 38B.

The proposed process for trial 38B is as follows:

1. Preparing a concentrated solution of Arsenic Trioxide by dissolving 4.00 gms of it in 20 ml of 3M sodium hydroxide solution. The expected pH of this solution would be around 13.2.

2. Adding 5.5 ml of 6 M HCl to partially neutralize the sodium hydroxide. The pH of the solution after partial neutralization should be around 9.0.

3. Separately, dissolving 40 mg of butylated hydroxytoluene in 18 ml of PEG 400. After obtaining a clear solution, mixing the entire content of BHT/PEG solution to 2 ml of partially neutralized Arsenic Trioxide solution. This should result in a clear solution which does not change color upon storage.

Details of Part 2 Experiments

Addition of glycerin was next investigated with the pH adjusted concentrated solution of ATO. 2 ml of each of the above pH adjusted concentrated solutions was mixed with 1.8 ml of glycerin and followed by the addition of 16.2 ml of PEG 400. Both the pH adjusted concentrated solutions (10.04 and 9.0) provided clear and colorless solutions upon mixing with glycerin and PEG 400.

Therefore, oral pharmaceutical formulations of Arsenic Trioxide particularly soft capsules of Arsenic Trioxide can be prepared with or without a co-solvent and with or without an antioxidant.

It shall be noted that currently approved dose for Arsenic Trioxide is 10 mg and accordingly, the soft capsule of the present invention preferably incorporates 10 mg dose and an appropriate amount of sodium hydroxide to keep this dose in dissolved form. This amount of sodium hydroxide causes discoloration of polyethylene glycol which is a very commonly used hydrophilic fill material. Various attempts have been made to avoid discoloration such as adding a co-solvent, adding an antioxidant and adjusting pH of the fill matrices etc. Even if by merely adjusting pH, one can reduce discoloration to a seemingly acceptable level, it may surface again upon storage and hence the present invention recommends use of co-solvent or antioxidant and not pH adjustment alone. Hence liquid fill matrix can include both a cosolvent and an antioxidant in addition to Arsenic Trioxide, sodium hydroxide solution, hydrochloric acid solution and fill material such as polyethylene glycol. Therefore. the oral pharmaceutical formulations of Arsenic Trioxide particularly soft capsules of Arsenic Trioxide can be prepared with both a co-solvent and an antioxidant.

However, it may be still possible to avoid discoloration if a very dilute solution of sodium hydroxide is employed to solubilize Arsenic Trioxide by merely adjusting pH and without adding a co-solvent or an antioxidant. This dilute solution however cannot dissolve the currently approved dose of Arsenic Trioxide but may dissolve lower doses such as 0.5 mg, 1 mg etc. Hence in future if such lower doses receive approvals, one can make an attempt to avoid discoloration by pH adjustment and without a co-solvent or an antioxidant.

Trials 39-42

Trial 39-42 investigated the order of pH adjustment and addition of cosolvent. These trials were conducted with PEG 600 as the fill material. Trial 39 utilizes glycerin as the cosolvent whereas Trial 40 uses propylene glycol. Similarly, Trial 41 is with glycerin and Trial 42 is with propylene glycol. For all four trials, first a concentrated solution of Arsenic Trioxide (540 mg/ml) is prepared using 6M NaOH. In trials 39 and 40; approximately 70% (~70%) of the base is neutralized by adding 6M HCl. The resulting pH of the solution is around 9.3 and the solution starts becoming turbid. To these turbid solutions, respective cosolvents (glycerin in trial 39 and propylene glycol in trial 40) are added followed by PEG 600. Both the trials provided a final clear and colorless solution.

In Trials 41 and 42, the cosolvents are first added to the concentrated Arsenic Trioxide solution and then the 6M solution of HCl is added. The order of addition in these two trials include first adding a cosolvent followed by hydrochloric acid solution to cause partial neutralization. The quantities are the same as in Trials 39 and 40. The resulting solutions, after partial neutralization, are clear and colorless. Thereafter, the volume is made up with PEG 600 and mixed thoroughly. The final solutions are clear and colorless. Technically, both the processes are feasible from the manufacturing point of view which means both the order of addition are acceptable but the preferred process would be to mix the concentrated Arsenic Trioxide solution first with the cosolvent and then with hydrochloric acid solution to partially neutralize it.

Therefore, ideal process for preparing fill matrix comprises
  i) preparing a first solution by dissolving Arsenic Trioxide in required amount of sodium hydroxide solution;
  ii) weighing required quantity of co-solvent;
  iii) preparing a second solution by mixing thoroughly Arsenic Trioxide solution and co-solvent;
  iv) adjusting pH if required by adding hydrochloric acid solution and mixing thoroughly to prepare a third solution; and
  v) preparing fourth and final solution viz. fill matrix by adding fill material polyethylene glycol and mixing thoroughly.

Each fill matrix can be used to prepare soft capsules of multiple doses by encapsulating different fill matrix weights in different sized capsules. Once, the fill matrix for higher dose is prepared, it can be diluted suitably to prepare lower dose formulations. Each diluted fill matrix formulation in the same way can be used to prepare soft capsules of multiple doses by encapsulating different fill matrix weights in different sized capsules. Trial 41 which can produce three doses of Arsenic Trioxide such as 20 mg, 10 mg and 5 mg by employing different fill matrix weight in different sized capsules (by dose weight proportion), after 1:1 dilution with fill material polyethylene glycol produces a first diluted formulation of fill matrix which provides three doses such as 10 mg, 5 mg and 2.5 mg by employing different fill matrix weights in different sized capsules. 1:1 dilution of this first diluted formulation by fill material polyethylene glycol produces a second diluted formulation of fill matrix which provides three doses such as 5 mg, 2.5 mg and 1 mg where doses of 5 mg, 2.5 mg and 1 mg are achieved by employing different fill matrix weights in different sized capsules.

Trial 32 had employed 0.625 parts of sodium hydroxide to dissolve 1 part of Arsenic Trioxide (ratio is 0.625:1) thus providing a solubility ratio of sodium hydroxide to Arsenic Trioxide as 1:1.6. It was further possible to lower the sodium hydroxide amount to a ratio of 1:4 as obtained in example 1. Fill matrices with sodium hydroxide to Arsenic Trioxide ratios of 1:4, 1:2 and 1:1.33 are provided in trials 45-48 which are exemplary trials. It is noted that although all fill matrices reported in trials 45-48 are feasible, some of the fill matrices have very high amounts of water and hence not advisable to use them for encapsulation.

In vegan soft capsule, almost the entire amount of water comes from sodium hydroxide solution as pH adjustment is not essential. As seen from trials 38A part 1 treatment, the role of pH adjustment is much bigger than just achieving a fill matrix which is compatible with the gelatin shell of the soft capsule. The pH adjustment plays a role in avoiding discoloration enabling preparation of fill matrix without co-solvent. Hence, even when matrices are prepared for vegan soft capsules, steps for pH adjustment could be followed to avoid discoloration while avoiding adding co-solvents.

In the above trials, water is contributed to the fill matrix from the use of aqueous solution of sodium hydroxide to dissolve Arsenic Trioxide; as well as aqueous solution of hydrochloric acid used for pH adjustment. Generally, the amount of hydrochloric acid solution required for adjusting pH in the range of 8.0-9.5 requires partial neutralization of sodium hydroxide added. For the same molarity of solutions of sodium hydroxide and hydrochloric acid, the volume of hydrochloric acid solution employed is around 70% of that of sodium hydroxide solution. Exemplary trials 45 to 48 provide volume of hydrochloric acid required for 70% neutralization of added sodium hydroxide. This is referred to as partial neutralization. It is preferred that water content does not exceed 20% w/w of the fill matrix. This does not however mean that lower molar solutions of sodium hydroxide cannot be employed. They are particularly useful for lower ratios of sodium hydroxide to Arsenic Trioxide where less amount of sodium hydroxide is required to dissolve lower doses of Arsenic Trioxide such as in trial 45.

It is possible to prepare fill matrices having Arsenic Trioxide in dissolved form for encapsulation in soft capsules wherein such matrices are with or without co-solvents like glycerin, wherein ratio of sodium hydroxide to Arsenic Trioxide can vary from 1:4 (or 0.25:1) to 1.625:1 or even beyond and wherein such matrices are with or without pH adjustment. It is possible to use sodium hydroxide from 0.1 part to 2 parts per part of Arsenic Trioxide to dissolve it and to keep it in dissolved form in the fill matrix.

It shall be understood that it is possible to use different ratios, different molar solutions, and different compositions of fill matrices and even different amounts of neutralizing solution for keeping Arsenic Trioxide in solution form; and the above trials provided are only few such trials from such a large number of possible trials. For example, exemplary trials 45-48 provided several formulations of fill matrices by only changing one parameter i.e., employing different solubility ratios of sodium hydroxide to Arsenic Trioxide having other parameters constant such as same amount of Arsenic Trioxide, polyethylene glycol and glycerin. Not all exemplary formulations might be suitable for encapsulation in the soft capsules.

Role of content of water on solubility of Arsenic Trioxide in sodium hydroxide solutions and role of glycerin/propylene glycol as co-solvents for Arsenic Trioxide are established in these trials. These agents are important and can be added cautiously in smaller quantities. Role of glycerin and propylene glycol is not only limited to its action as a co-solvent in a fill matrix but in also avoiding discoloration.

Further, formulations of fill matrices may include one or more of Surfactants, absorption enhancers and crystal growth inhibitors such as sodium polyacrylate, polyvinyl pyrrolidone (PVP) having a k value from 10 to 120, Macrogol 15 Hydroxystearate (SOLUTOL™), Propylene Glycol Caprylate (CAPRYOL™) and Polyoxyl 40 Hydrogenated Castor Oil. These ingredients may further reduce the ratio of sodium hydroxide to Arsenic Trioxide or further reduce the requirement of a co-solvent.

Thus, combination of sodium hydroxide solution, hydrochloric acid solution, glycerin or propylene glycol and polyethylene glycol provide one of the simplest formulations to keep Arsenic Trioxide in dissolved form for ready incorporation into a soft capsule. Both cosolvent and water which is added from solutions of sodium hydroxide and hydrochloric acid are kept as low as possible.

In preferred embodiments water (derived from sodium hydroxide and hydrochloric acid solutions) and glycerin or propylene glycol are employed in weight ratio from 5:1 to 1:10 and preferably from 2:1 to 1:5 and most preferably from 1:1 to 1:3.

Combination without co-solvent is also possible where sodium hydroxide solution, hydrochloric acid solution and polyethylene glycol also provide one of the simplest formulations to keep Arsenic Trioxide in dissolved form for ready incorporation into a soft capsule. However, considering possible later color development, an antioxidant addition is recommended in such formulations.

The trials 1 to 42 facilitated arriving at suitable formulations of fill matrices of Arsenic Trioxide containing it in dissolved form. These trials also facilitated arriving at a suitable process of preparation of fill matrices. These fill matrices are suitable for encapsulation into soft capsules.

Preparing appropriate fill matrix suitable for soft capsule shell as well as for keeping Arsenic Trioxide in a dissolved state was a big challenge which has been accomplished successfully in the present invention. The soft capsules of the present invention can conveniently deliver doses from 0.1 mg to 25 mg of Arsenic Trioxide, preferably from 1 mg to 25 mg and more preferably from 1 mg to 20 mg of Arsenic Trioxide.

In an embodiment, a soft capsule delivers a dose of 1 mg. Another embodiment, a soft capsule delivers a dose of 20 mg. Various embodiments of the present invention deliver 1 mg, 2.5 mg, 5 mg, 10 mg, 20 mg, 25 mg doses of Arsenic Trioxide. Two capsules of 25 mg can provide a total dose of 50 mg. One capsule of 25 mg four times a day can provide a total daily dose of 100 mg. None of the indications approved or under trials has prescribed such high daily doses of Arsenic Trioxide as 50 or 100 mg. Nevertheless, if in future such doses are indicated, the soft capsules of the present invention can incorporate the same.

In terms of percent W/W, the amounts of Arsenic Trioxide in a total fill weight of a soft capsule are from 0.1% to 10%. In an embodiment, Arsenic Trioxide is present in an amount of 1.86% of the fill matrix. In another embodiment, Arsenic Trioxide is present in an amount of 0.92% of the fill matrix. In preferred embodiments, Arsenic Trioxide is present in an amount from 0.2-5%, preferably from 0.4 to 2% and more preferably from 0.459%-1.86% of the fill matrix.

The preferred solubilizing/alkalizing agent is sodium hydroxide employed in the form of its aqueous solution. 1M to 6 M solutions of sodium hydroxide are preferred. 3M to 6 M solutions of sodium hydroxide are most preferred. In various embodiments, from 0.25 parts to 1.625 parts, more preferably from 0.4 to 1.375 parts and most preferably from 0.4-0.875 parts of sodium hydroxide per part of Arsenic Trioxide are employed. It is possible to use sodium hydroxide from 0.1 part to 2 parts per part of Arsenic Trioxide. In a few embodiments, 0.6 parts per part of Arsenic Trioxide is employed. Most preferably, 0.44 parts of sodium hydroxide per part of Arsenic Trioxide is employed. Preferably, the embodiments employed from 1M-6M solution of sodium hydroxide to dissolve Arsenic Trioxide. The resulting Arsenic Trioxide solution has a high pH and pH of the resultant fill matrix is also high and may not be suitable for incorporation into a soft gelatin capsule although there is no restriction of pH in case of a vegan soft capsule. Accordingly, pH adjustment with a neutralizing agent may be necessary. The pH is preferably adjusted in a range of 8.0-9.5 for encapsulation in a soft gel capsule, preferably in the range of 9-9.5 This is termed as partial neutralization. The preferred neutralizing agent is hydrochloric acid. Solution of 1M to 6M Hydrochloric acid is employed to adjust pH of solution within a range suitable. Also, since vegan soft capsule can encapsulate fill matrices of high pH, neutralizing agents are not essential in fill matrices for encapsulation in vegan soft capsule. Once the pH is near the desired pH range, further pH adjustment is done with dilute hydrochloric acid to avoid huge swing in pH. The pH of the final fill matrix for encapsulation into a soft gelatin capsule is preferably not less than 8 and not more than 9.5. Preferably, the pH is from 8.0-9.5 and more preferably from 8.5-9.5 and most preferably around 9.0 or from 9.0 to 9.5.

Amounts of sodium hydroxide solution and hydrochloric acid solution should be such that the water being added from such solution in the final fill matrix should not rise beyond a certain amount which is not more than 20%, more preferably not more than 15% and most preferably not more than 10% of the fill matrix. A fill matrix with higher amounts of water is undesirable for encapsulation in a soft capsule. In few preferred embodiments, water is from 8-9% of the fill matrix. In a few other embodiments, water is from 5-6% of the fill matrix. Few more embodiments have water content below 5% such as 1%, and 2%.

Soft capsules of the present invention employ at least 80% of nonaqueous component. This component is predominantly hydrophilic and mainly comprises of hydrophilic fill material and a hydrophilic co-solvent.

Polyethylene glycol is preferred fill material. It can also be employed as co-solvent. The total amount of Polyethylene glycol can be divided into two portions/parts. First portion/part is around 5-30% and the second portion/part is around 70-95% of the total amount. First smaller portion can be used as a cosolvent whereas the second larger portion can be used as a fill material.

Alternatively, polyethylene glycols of two different grades are employed. High molecular weight grades such as PEG 600, PEG 800 or PEG 1000 are employed as cosolvents and PEG 400 is used as a fill material.

When polyethylene glycol is also used as a cosolvent, other cosolvent may or may not be needed. Still adding cosolvent is desired. The fill matrix in addition to Arsenic Trioxide, sodium hydroxide (solubilizer/solubilizing agent) and Hydrochloric acid (Neutralizing agent), polyethylene glycol (fill material) may comprise one or more co-solvents and antioxidants and also optionally one or more of surfactants, absorption enhancers and crystal growth inhibitors.

Role of co-solvents was multifold and was evident in most trials. It reduced the amount of solubilizing agent required to solubilize Arsenic Trioxide and avoided discoloration. Both glycerin and propylene glycol are found suitable as co-solvents.

The inventor has tried different amounts of cosolvent Glycerin from 1-70% but a fill matrix suitable for encapsulation has not more than 20%, preferably not more than 15% and most preferably not more than 10% of glycerin of the total fill matrix. These trials are reported under example 7.

In preferred embodiments, water and glycerin/propylene glycol are added in a weight ratio of 5:1 to 1:10, preferably from 2:1 to 1:5 and most preferably from 1:1 to 1:3. In a preferred embodiment, water and glycerin are added in a weight ratio of 1:1 to 1:3. In a few embodiments, water and glycerin are added in a weight ratio of from 1:3 to 1:6. In yet another embodiment, water and glycerin are added in a weight ratio from 1:6 to 1:8.

One or more further solvents can be added while preparing the liquid fill matrix and the solvent is selected from benzyl alcohol, ethylene glycol phenyl ether, propylene glycol, propylene glycol phenyl ether, propylene carbonate, phenoxyethanol, dimethyl malonate, dimethyl succinate, diethyl succinate, dibutyl succinate, TRANSCUTOL™ P, dimethyl glutarate, diethyl glutarate, dibutyl glutarate, dimethyl adipate, diethyl adipate, dibutyl adipate or any combination thereof.

Additionally, formulation of present invention may include one or more of surfactants, absorption enhancers and crystal growth inhibitors such as sodium polyacrylate, polyvinyl pyrrolidone (PVP) having a k value from 10 to 120, Macrogol 15 Hydroxystearate (SOLUTOL™), Propylene Glycol Caprylate (CAPRYOL™) and Polyoxyl 40 Hydrogenated Castor Oil.

In an embodiment, sodium polyacrylate is incorporated up to 2% by weight of the fill matrix. In few embodiments, PVP K30 is incorporated in amounts of 0.1%, 0.25%, 0.5%, 0.75%, 1.0%, 1.3755%, 1.5%, 1.75% and 2% W/W of the fill matrix. In a few other embodiments, Macrogol 15 Hydroxystearate (SOLUTOL™) is employed from 0.1% to up to 5% preferably from 0.5-2.0% W/W of the fill matrix.

An embodiment of prepared fill matrix according to the present invention is encapsulated in a soft capsule wherein the liquid fill matrix is without any surfactant, absorption enhancer, crystal growth inhibitor. Similarly, another embodiment of prepared fill matrix according to the present invention is filled in a capsule wherein fill matrix has at least one of the surfactant, absorption enhancer, crystal growth inhibitor. Both capsules are subjected to dissolution testing using 900 ml of 0.1N HCl. Both the liquid fill matrices upon subjected to 900 ml of 0.1N HCl, do not show any kind of precipitation.

In the present invention, the solubilization of Arsenic Trioxide therefore does not depend on one or more of surfactant, absorption enhancer and crystal growth inhibitor.

The present invention arrives at a suitable dosage form for Arsenic Trioxide which is safe, self-administrable, patient compliant, cost effective and where issues of solubility and dissolution rates are addressed, and thereby bioavailability are resolved.

Purposes of designing new dosage form of Arsenic Trioxide are to provide safer dosage form to avoid direct contact with Arsenic Trioxide and to provide solid oral dosage form which can be self-administered having Arsenic Trioxide in dissolved form. Arsenic Trioxide remains in dissolved form even after ingestion. Presence or absence of precipitation of Arsenic Trioxide from a liquid fill matrix containing dissolved Arsenic Trioxide when subjected to 0.1N HCl may indicate precipitation or no precipitation of Arsenic Trioxide in acidic conditions of the stomach and if it is precipitated, it will be far more difficult to redissolve. In example 7, fill matrix containing dissolved Arsenic Trioxide encapsulated in hard gelatin capsule are subjected to dissolution in 900 ml of 0.1 N HCl with stirring (Type 2: paddles; 50 RPM) to simulate gastric conditions and no precipitation/solid form separation of Arsenic Trioxide was observed. The fill matrix when subjected to manifold dilution with a media of acidic pH did not cause precipitation of Arsenic Trioxide from its dissolved form. Therefore, Arsenic Trioxide dissolved in the liquid fill matrix of the present invention will continue to remain in dissolved state even after ingestion.

The present invention further provides the process of preparing a soft capsule comprising preparation of a fill matrix and encapsulating fill matrix to prepare soft capsule. Two major problems were identified which were i) very low solubility of Arsenic Trioxide in polyethylene glycol which is a preferred fill material and a major ingredient of a nonaqueous component which is at least 80% of the fill matrix. and ii) discoloration or yellow to reddish brown color formation due to interactions between polyethylene glycol and sodium hydroxide solution.

Adding a co-solvent such as glycerin or propylene glycol enhanced solubility of Arsenic Trioxide in the fill matrix and also avoided discoloration when employed in specific order of addition.

The present invention provides that by merely changing the sequence of addition of various ingredients, discoloration can be prevented, and invention further provides a process of preparation of fill matrix containing dissolved Arsenic Trioxide where such fill matrix can be conveniently encapsulated in soft gelatin or vegan soft capsule.

pH adjustment also plays a role in avoiding discoloration and a colorless clear fill matrix can be prepared even without a co-solvent. Additionally, an antioxidant can be added to prevent color development if any on storage.

Trials 1-42 also facilitated arriving at three different processes that can be used to successfully prepare a liquid fill matrix having Arsenic Trioxide in dissolved form wherein two processes are for preparing the liquid fill matrix containing a cosolvent whereas the third process is for preparing the liquid fill matrix without a cosolvent and with an antioxidant. Alternatively, a fourth process can also be used for preparing a liquid fill matrix having both a cosolvent and an antioxidant. All processes employ first preparing Arsenic Trioxide solution using sodium hydroxide. This solution is either added to a co-solvent and then pH is adjusted or first a pH adjustment is done and then such pH adjusted solution is added to a co-solvent. Finally fill material is added. To avoid co-solvent, Arsenic Trioxide solution prepared by using sodium hydroxide is first subjected to a pH adjustment to around 9. A suitable antioxidant is dissolved in polyethylene glycol and this solution is added to pH adjusted solution of Arsenic Trioxide.

Figure 2A:
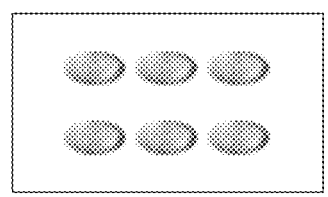
FIG. 2A provides soft gelatin capsules containing 10 mg Arsenic Trioxide.
Figure 2B:
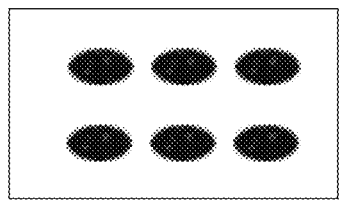
FIG. 2B provides soft gelatin capsules containing 5.0 mg Arsenic Trioxide.
Figure 2C:
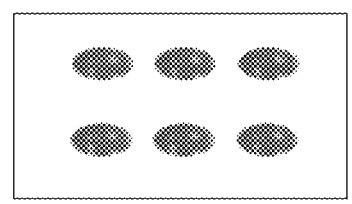
FIG. 2C provides soft gelatin capsules containing 2.5 mg Arsenic Trioxide.

Table 1 provides a general composition of the liquid fill matrix according to the present invention for encapsulation into a soft capsule of the present invention. Tables 2, 3 and 4 provide various preferred pharmaceutical formulations of liquid fill matrices according to the present invention. A soft gelatin capsule encapsulating liquid fill matrix formulation of table 2 containing 10 mg of Arsenic Trioxide has been prepared and shown in FIG. 2A. A soft gelatin capsule encapsulating liquid fill matrix formulation of Table 3 containing 5 mg of Arsenic Trioxide has been prepared and shown in FIG. 2B. A soft gelatin capsule encapsulating liquid fill matrix formulation of Table 4 containing 2.5 mg of Arsenic Trioxide has been prepared and shown in FIG. 2C.

TABLE 1

General composition of liquid fill matrix according to the present invention.

| Ingredient | Function | Range |
| --- | --- | --- |
| Arsenic Trioxide | Active Pharmaceutical Ingredient | 0.1-25 mg; from 0.1-10 Weight % of fill matrix; preferably from 0.2-5 Weight % of fill matrix and more preferably from 0.4 to 2 Weight % of fill matrix |
| Sodium hydroxide | Solubilizing agent/ Solubilizer | from 0.1 part to 2 parts per part of Arsenic Trioxide; preferably from 0.25-1.625 parts per part of Arsenic Trioxide, more preferably from 0.4-1.375 parts per part of Arsenic Trioxide and most preferably from 0.4-0.875 parts per part of Arsenic Trioxide. |

TABLE 1-continued

General composition of liquid fill matrix according to the present invention.

| Ingredient | Function | Range |
| --- | --- | --- |
| Hydrochloric acid | Neutralizing agent | Quantity sufficient to adjust pH in the range of 8-9.5 for fill matrix which is for encapsulation in a soft gel capsule and<br>Quantity sufficient to adjust pH in the range of 8-12.5 for fill matrix which is for encapsulation in a vegan soft capsule |
| Nonaqueous component Fill material preferably PEG 400/PEG 600 in nonaqueous component | Fill material | At least 80% of a liquid fill matrix.<br>At least 60% of the liquid fill matrix, preferably at least 70% of the liquid fill matrix. |
| Water | From aqueous solutions of sodium hydroxide and hydrochloric acid | Water to Glycerin in a weight ratio preferably from 5:1 to 1:10, more preferably from 2:1 to 1:5 and most preferably from 1:1 to 1:3 wherein each is employed preferably below 20%, more preferably below 15% and most preferably below 10% W/W of the fill matrix. |
| Glycerin or propylene glycol | plays the role of a cosolvent in the fill matrix, also helps to prevent discoloration. | |
| Antioxidant | plays a role to prevent discoloration. | 0.0-2% |
| Optional ingredients: sodium polyacrylate, polyvinyl pyrrolidone (PVP) having a k value from 10 to 120, Macrogol 15 Hydroxystearate (SOLUTOL ™), Propylene Glycol Caprylate (CAPRYOL ™) and Polyoxyl 40 Hydrogenated Castor Oil. | Surfactants, absorption enhancers and crystal growth inhibitors | When present, the suitable range is from 0.1-2% by weight of the fill matrix. |

Compositions in mg per unit soft capsule of most preferred formulations are provided in Tables 2-4 below and most preferred process of preparing liquid fill matrices is also described.

TABLE 2

Fill Matrix Size for 20 mg, 10 mg and 5 mg Arsenic Trioxide

| Ingredient | Range in Mg/ Liquid Fill Matrix of soft capsule | Ingredients % W/W for an embodiment from provided range. | % Of Aqueous and nonaqueous components |
| --- | --- | --- | --- |
| Arsenic Trioxide | 5-20 | 1.86 | Total Aqueous component is 7.72% |
| Sodium hydroxide | 2-17.5 | | |
| Sodium hydroxide solution | | 3.45 | |
| Hydrochloric acid | 1-14 | | |
| Hydrochloric acid solution | | 2.41 | |
| Water | 10-50 | | |
| PEG 400/PEG 600 | 200-900 | 81.72 | Total nonaqueous component is 92.28% |
| Glycerin | 20-150 | 10.56 | |
| Butylated Hydroxy Toluene | 0-18 | | |
| Total Weight | 238-1169.5 | | |
| Total volume | 0.2-1.2 ml | | |
| Suitable capsule size | 4-5 oblong to 20-22 oblong | | |

TABLE 3

Fill Matrix Size for 10 mg, 5 mg and 2.5 mg Arsenic Trioxide

| Ingredient | Range Mg/ Liquid Fill Matrix of soft capsule | Ingredients % W/W for an embodiment from provided range. | % Of aqueous and nonaqueous components |
|---|---|---|---|
| Arsenic Trioxide | 2.5-10 | 0.93 | Total Aqueous component is 3.86% |
| Sodium hydroxide | 1-8.75 | | |
| Sodium hydroxide solution | | 1.72 | |
| Hydrochloric acid | 0.5-6.56 | | |
| Hydrochloric acid solution | | 1.21 | |
| Water | 5-25 | — | |
| PEG 400/PEG 600 | 200-1000 | 90.86 | Total nonaqueous component is 96.14% |
| Glycerin | 10-75 | 5.28 | |
| Butylated Hydroxy Toluene | 0-20 | | |
| Total Weight | 219-1145.31 | | |
| Total volume | 0.2-1.2 ml | | |
| Suitable capsule size | 4-5 oblong to 20-22 oblong | | |

TABLE 4

Fill Matrix Size for 2.5 mg and 1 mg Arsenic Trioxide

| Ingredient | Range in Mg/ Liquid Fill Matrix of soft capsule | Ingredients % W/W for an embodiment from provided range. | % Of aqueous and nonaqueous components |
|---|---|---|---|
| Arsenic Trioxide | 1-2.5 | 0.47 | Total Aqueous component is 1.93% |
| Sodium hydroxide | 0.4-2.19 | | |
| Sodium hydroxide solution | | 0.86 | |
| Hydrochloric acid | 0.2-1.64 | | |
| Hydrochloric acid solution | | 0.60 | |
| Water | 2-10 | | |
| PEG 400 | 150-600 | 95.43 | Total nonaqueous component is 98.07% |
| Glycerin | 4-30 | 2.64 | |
| Butylated Hydroxy Toluene | 0-12 | | |
| Total Weight | 157.6-658.33 | | |
| Total volume | 0.15 ml-0.6 ml | | |
| Suitable capsule size | 4-5 oblong to 9.5-11 oblong | | |

Process for Preparing Soft Capsules of Table 2, 3 and 4

A sequence "b" or "d" is selected having process steps i, ii, iv, v and vii or i, ii, iv, v and vii. The sequence "d" enables addition of an antioxidant in above compositions.

6 molar aqueous solutions of sodium hydroxide and hydrochloric acid are prepared. Amount of sodium hydroxide used is selected from 0.4 to 0.875 parts per part of Arsenic Trioxide. Particularly the amount is selected from 0.875, 0.7, 0.625, 0.6, 0.54, 0.5, 0.48, 0.44 and 0.4 parts of sodium hydroxide per part of Arsenic Trioxide is selected. Arsenic Trioxide is dissolved in a solution of sodium hydroxide and mixed thoroughly. Co-solvent glycerin is added in amounts from 1-15% of the total fill matrix and mixed thoroughly. Partial neutralization is done by adding from around 50-80% moles of hydrochloric acid of the total moles of sodium hydroxide added so that the pH is around 9 and mixed thoroughly. Water added from aqueous solutions of sodium hydroxide and hydrochloric acid is from 1-5% of the fill matrix. Polyethylene glycol 400 or 600 is added in amounts of at least 60% of the fill matrix, preferably in amounts of at least 70% and at least 80% and at least 90% for different doses and mixed thoroughly.

Following examples describe the invention and do not limit the scope of the invention in any way. It is further possible to change all parameters one by one or simultaneously and make hundreds and thousands of formulations all of which will fall within the scope of the present invention. While setting limits on the amounts of various ingredients, it is not essential that amounts beyond the said limit does not work. For example, even if for sodium hydroxide preferred lower and upper limits are mentioned, it is understood that an amount above 1.625 parts per part of Arsenic Trioxide (>650 mg for 400 mg of Arsenic Trioxide) can certainly dissolve Arsenic Trioxide. Also, if a fill matrix containing 70% fill material is encapsulated, it is certainly possible to encapsulate a fill matrix having 60 or 65% of fill material. Similarly, ratio of water to glycerin is mentioned merely to enable easy preparation of liquid fill matrix for soft capsules.

It shall be noted that the words preferred, preferably, more preferred or more preferably and most preferred and most preferably merely convey selection of ingredients or ingredients and their quantities from among the large workable range. The present invention makes an attempt to arrive at suitable soft gel capsules encapsulating various liquid fill matrices containing Arsenic Trioxide in dissolved form and limiting the invention only to certain embodiment or example is not intended.

EXAMPLES

Example 1: Solubilization of Arsenic Trioxide in the Presence of Hydroxides

TABLE 5

| Ingredient | Trial 1 | Trial 2 | Trial 3 | Trial 4 | Trial 5 | Trial 6 | Trial 7 | Trial 8 | Trial 9 | Trial 10 |
|---|---|---|---|---|---|---|---|---|---|---|
| NaOH (mg) | 100 | 150 | 200 | 250 | 300 | 400 | 500 | 550 | 600 | 650 |
| Arsenic Trioxide (mg) | 400 | 400 | 400 | 400 | 400 | 400 | 400 | 400 | 400 | 400 |
| Water (ml) | 20 | 20 | 20 | 20 | 20 | 20 | 20 | 20 | 20 | 20 |
| Observation | CCS* | CCS* | CCS* | CCS* | CCS* | CCS* | CCS* | CCS* | CCS* | CCS* |
| Final pH | 9.4 | 10.26 | 12.47 | 12.99 | 13.23 | 13.39 | 13.51 | 13.6 | 13.6 | 13.6 |
| Ratio NaOH to ATO | 1:4 | 1:2.67 | 1:2 | 1:1.6 | 1:1.33 | 1:1 | 1:0.8 | 1:0.73 | 1:0.67 | 1:0.62 |

CCS*—Clear Colorless Solution,
ND**—Not determined

Process: 10 vials were taken and 20 ml of purified water added in each vial. To each vial required a quantity of NaOH was added as mentioned in the above table. Observation was noted and pH was measured. To each vial, 400 mg of Arsenic Trioxide was added and shaken to dissolve. Then description was noted, and pH was measured.

Conclusion: For preparing an aqueous solution of Arsenic Trioxide; the ratio of NaOH to Arsenic Trioxide should be at least 1:4 OR 0.25:1. Higher ratio of NaOH to Arsenic Trioxide (more than 1:4) lowers the pH aqueous solution and does not dissolve Arsenic Trioxide. The said aqueous solution is of desired strength but cannot be used for encapsulation in soft capsules.

Example 2: Solubilization of Arsenic Trioxide in the Pretreated PEG 400 with Hydroxide

TABLE 6A

| Ingredient | Trial 11 | Trial 12 | Trial 13 | Trial 14 | Trial 15 |
|---|---|---|---|---|---|
| PEG 400 (75% of theoretical qty) ml | 14.7 | 14.5 | 14.4 | 14.2 | 14.1 |
| NaoH (mg) | 100 | 150 | 200 | 250 | 300 |
| Volume of 6M NaOH | 0.42 | 0.62 | 0.83 | 1.04 | 1.25 |
| Final Water Content of Formulation (%) | 2.1 | 3.1 | 4.15 | 5.2 | 6.25 |
| Observation | Clear, light yellow Colored solution | Clear, light yellow Colored Solution | Clear, Yellow Colored Solution | Clear, Yellow Colored Solution | Clear, Yellow Colored Solution |
| Arsenic Trioxide (mg) | 400 | 400 | 400 | 400 | 400 |
| Add remaining qty of PEG 400 (ml) | 4.9 | 4.8 | 4.8 | 4.7 | 4.7 |
| Total Volume (ml) | 20 ml | 20 ml | 20 ml | 20 ml | 20 ml |
| Final Observation | Insoluble | Insoluble | Slightly soluble | Slightly soluble | Sparingly soluble |
| Ratio NaOH to Arsenic Trioxide | 1:4 | 1:2.67 | 1:2 | 1:1.6 | 1:1.33 |

Example 2: Solubilization of Arsenic Trioxide in the Pretreated PEG 400 with Hydroxide (Continued)

TABLE 6B

| Ingredient | Trial 16 | Trial 17 | Trial 18 | Trial 19 | Trial 20 |
|---|---|---|---|---|---|
| PEG 400 (75% of theoretical qty) ml | 13.7 | 13.4 | 13.4 | 13.1 | 13.0 |
| NaoH (mg) | 400 | 500 | 550 | 600 | 650 |
| Volume of 6M NaOH | 1.60 | 2.10 | 2.20 | 2.50 | 2.70 |

TABLE 6B-continued

| Ingredient | Trial 16 | Trial 17 | Trial 18 | Trial 19 | Trial 20 |
|---|---|---|---|---|---|
| Final Water Content of Formulation | 8 | 10.5 | 11 | 12.5 | 13.5 |
| Observation | Clear, Deep Yellow Colored Solution | Clear, Yellowish-Orange Colored Solution | Clear, Yellowish-Orange Colored Solution | Clear, Reddish-brown Colored Solution | Clear, Reddish-brown Colored Solution |
| Arsenic Trioxide (mg) | 400 | 400 | 400 | 400 | 400 |
| Add remaining qty of PEG 400 (ml) | 4.6 | 4.5 | 4.4 | 4.4 | 4.3 |
| Total Volume (ml) | 20 ml | 20 ml | 20 ml | 20 ml | 20 ml |
| Final Observation | Sparingly soluble | Sparingly soluble | Completely soluble | Completely soluble | Completely soluble |
| Ratio NaOH to Arsenic Trioxide | 1:1 | 1:0.8 | 1:0.73 | 1:0.67 | 1:0.62 |

Process: 10 vials were taken and 75% of theoretical quantity of PEG 400 was added in each vial as detailed in above table for each trail. To each vial required qty. of 6M NaOH solution (240 mg/ml) was added. Water comes from the 6M solution of NaOH. Observation was noted. To each vial 400 mg of Arsenic Trioxide was added and shaken. Remaining 25% of PEG 400 was added to each vial and shaken to dissolve.

Observation was noted.

Conclusion: Arsenic Trioxide can be dissolved in pretreated PEG 400 with the sodium hydroxide. However, the amount of sodium hydroxide needed is much higher. The minimum ratio of NaOH to Arsenic Trioxide is 1:0.73 OR 1.37:1 in the PEG 400. Also, pretreatment of PEG 400 with such high amounts of sodium hydroxide leads to discoloration of PEG 400. Even though the desired concentration of Arsenic Trioxide, in the solution form, is achieved in PEG 400—it is not an ideal solution for encapsulation due to discoloration.

Example 3: Improving the Solubilization Ratio of NaOH to Arsenic Trioxide in Pretreated PEG 400 with Hydroxides Using Water Content The following experiment was conducted using 3M NaOH instead of 6M NaOH used in Example 2.

TABLE 7

| Sr. No. | Ingredient | Trial 21 | Trial 22 | Trial 23 | Trial 24 |
|---|---|---|---|---|---|
| 1 | PEG 400 (75% of theoretical qty) in ml | 14.37525 | 14.0625 | 13.7505 | 13.437525 |
| 2 | Sodium Hydroxide (mg) | 100 | 150 | 200 | 250 |
| 3 | Volume of 3M NaOH solution added (ml) drop by drop for the required amount of NaOH under magnetic bead stirring | 0.83 | 1.25 | 1.67 | 2.08 |
| | Observation (after 10-15 mins of addition) | Light yellow colored solution | Light yellow colored solution | yellow colored solution | yellow colored solution |
| | Addition of Arsenic Trioxide (400 mg) | | | | |
| 4 | Arsenic Trioxide | 400 mg (20 mg/ml) | 400 mg (20 mg/ml) | 400 mg (20 mg/ml) | 400 mg (20 mg/ml) |
| 5 | Remaining quantity of PEG 400 in ml | 4.79175 | 4.6875 | 4.5835 | 4.479175 |
| | PEG 400 theoretical qty in ml | 19.17 | 18.75 | 18.33 | 17.92 |
| 6 | Total Volume | 20 ml | 20 ml | 20 ml | 20 ml |
| | Stirring time (By magnetic bead) | 1 hr | 1 hr | 1 hr | 1 hr |
| | Solubility of Arsenic Trioxide (After 24 hours) | Not soluble | Not soluble | Not soluble | Soluble |
| | Color of vehicle after addition of Arsenic Trioxide (after 24 hrs) | Light yellow colored solution | Light yellow colored solution | Clear yellow colored solution | Clear yellow colored solution |
| | Final Water content of the formulation (%) | 4.15 | 6.25 | 8.35 | 10.4 |
| | Ratio of NaOH to Arsenic Trioxide | 1:4 | 1:2.67 | 1:2 | 1:1.6 |

Process: Prepare 3M NaOH solution in purified water (120 mg/ml) and take 75% of the theoretical volume of PEG 400 in a vial. Add the needed volume of 3M NaOH drop by drop under magnetic stirring to the PEG 400; Mix thoroughly with magnetic stirrer; check the clarity and color of the solution. Then add 400 mg of Arsenic Trioxide to each vial; shake gently so that the Arsenic Trioxide particles do not stick to the vial or cap. Add the remaining 25% amount of PEG 400. Each vial was stirred by magnetic bead for 1 hr and solubility of Arsenic Trioxide was noted down.

Conclusion: The solubilization ratio of NaOH to Arsenic Trioxide was improved from 1:0.73 (example 2) to 1:1.6 OR (1.37:1 to 0.86:1) by increasing the water content to 10.4% of the final solution.

Example 4: Pretreatment of PEG 400 with Antioxidant Before Adding Hydroxides

TABLE 8

| Sr. No. | Ingredient | Trial 25 | Trial 26 |
|---|---|---|---|
| 1 | PEG 400 (75% of theoretical qty) in ml | 13.3 | 13.3 |
| 2 | Sodium Hydroxide (mg) | 550 | 550 |
| 3 | Volume of 6M NaOH solution added for the required amount of NaOH | 2.20 | 2.20 |
| 4 | Addition of BHT (butylated hydroxy toluene) | 0.20% | 2.00% |
| Description (after 10-15 mins of addition) | | Clear, Low intensity Yellowish-Orange Colored Solution | Clear, Low intensity Yellowish-Orange Colored Solution |

Process: BHT (butylated hydroxy toluene) was added to PEG 400. Once it was completely in solution, the required quantity of sodium hydroxide was added to the solution. Upon stirring, the solution started changing color to yellowish orange color. The intensity of the color was significantly less as compared to the color observed in Example 2.

Conclusion: An antioxidant can be used to prevent any color formation in the PEG based fill material.

Example 5: Replacement of PEG 400 with Glycerin

TABLE 9

| Sr. No. | Ingredient | Trial 27 | Trial 28 |
|---|---|---|---|
| 1 | PEG 400 (75% of theoretical qty) in ml | 13.44 | 0.0 |
| | Glycerin (75% of theoretical qty) in ml | 0.0 | 13.44 |
| 2 | Sodium Hydroxide (mg) | 250 | 250 |
| 3 | Volume (ml) of 3M NaOH solution added drop by drop under magnetic bead stirring | 2.08 | 2.08 |
| | Description (after 10-15 mins of addition) | yellow colored solution | CCS |
| 4 | Arsenic Trioxide | 400 mg | 400 mg |
| 5 | Remaining quantity of PEG 400 in ml | 4.48 | — |
| | PEG 400 theoretical qty in ml | 17.92 | — |
| | Remaining quantity of Glycerin in ml | — | 4.48 |
| | Glycerin theoretical quantity in ml | — | 17.92 |
| 6 | Total Volume | 20 ml | 20 ml |
| | Stirring time (By magnetic bead) | 1 hr | 1 hr |
| | Solubility of Arsenic Trioxide | Soluble | Dissolved slowly on standing for few hrs. |
| | Description after addition of Arsenic Trioxide (after 24 hrs) | Clear yellow colored solution | Clear colorless solution on standing for few hrs. |
| | Final Water content of the formulation (%) | 10.4 | 10.4 |

CCS—Clear Colorless Solution

Process: Example 2 was repeated with the replacement of PEG 400 with glycerin because of the color formation with PEG 400. Hence in both these trials, pretreatment of PEG or Glycerin with sodium hydroxide is done before dissolving Arsenic Trioxide. Trial 28 where PEG is replaced with glycerin and Glycerin is pretreated with sodium hydroxide before dissolving Arsenic Trioxide did not exhibit discoloration. However, it did not yield a clear solution first but on standing for few hrs, a clear solution is obtained.

Process: The experiment with glycerin as mentioned in Example 5 was repeated but the order of addition of the various components was changed. First Arsenic Trioxide was dissolved in 3M NaOH to prepare a concentrated solution of Arsenic Trioxide instead of pretreating glycerin with sodium hydroxide as done in trial 28. Subsequently, glycerin was added. It was discovered that in all three trials crystal clear solutions were obtained. These solutions did not change color upon storage. However, 100% glycerin solutions are not suitable for encapsulation in soft capsule.

Example 6: Order of Mixing with Glycerin

TABLE 10

| Sr. No. | Ingredient | Trial 29 | Trial 30 | Trial 31 |
|---|---|---|---|---|
| 1 | Sodium Hydroxide (mg) | 250 | 300 | 350 |
| 2 | Volume of 3M NaOH solution added(ml) drop by drop for the required amount of NaOH under magnetic bead stirring | 2.08 | 2.50 | 2.91 |
| | Addition of Arsenic Trioxide (400 mg) under stirring | | | |
| 3 | Arsenic Trioxide | 400 mg (192.30 mg/ml) | 400 mg (160 mg/ml) | 400 mg (137.45 mg/ml) |
| | Stirring time (By magnetic bead) | 30 mins | 20 mins | 15 mins |
| | Solubility of Arsenic Trioxide | Soluble | Soluble | Soluble |
| 4 | Glycerin qty added in ml | 17.92 | 17.50 | 17.09 |
| 5 | Total Volume | 20 ml | 20 ml | 20 ml |
| | Stirring time (By magnetic bead) | 30 mins | 30 mins | 30 mins |
| | Solubility of Arsenic Trioxide | Soluble | Soluble | Soluble |
| | Final Concentration of Arsenic Trioxide in solution | 20 mg/ml | 20 mg/ml | 20 mg/ml |
| | Description after addition of Glycerin and 30 mins stirring | Clear solution, No color change | Clear solution, No color change | Clear solution, No color change |

Example 7: Fill Matrix with Combination of PEG and Glycerin with Revised Order of Mixing

TABLE 11

| Sr. No. | Ingredient Name | Trial 32A | Trial 33 | Trial 34 | Trial 35 |
|---|---|---|---|---|---|
| 1 | Sodium Hydroxide Solution taken | 3M | 3M | 3M | 3M |
| | Qty. of NaOH solution taken | 2 | 2 | 2 | 2 |
| 2 | Qty. of NaOH present in solution | 240 mg | 240 mg | 240 mg | 240 mg |
| | pH of NaOH solution (without Arsenic Trioxide) | 14.5 | 14.5 | 14.5 | 14.5 |
| 3 | Addition of Arsenic Trioxide | 400 mg | 400 mg | 400 mg | 400 mg |
| | Stirring time | 30 mins | 30 mins | 30 mins | 30 mins |
| 4 | Qty. of Glycerin taken | 1.8 ml (1 Part) | 5.4 ml (3 Parts) | 9 ml (5 Parts) | 12.6 ml (7 Parts) |
| 5 | Qty. of PEG 400 taken | 16.2 ml (9 Parts) | 12.6 ml (7 Parts) | 9 ml (5 Parts) | 5.4 ml (3 parts) |
| | Initial observation | Clear yellowish solution | Clear slight yellowish solution | Clear colorless solution | Clear colorless solution |
| | Observation (After 24 hrs) | Clear yellow colored solution | Yellowish colored solution | Slight yellowish colored solution | Very slight yellowish colored solution |

Process: Following four formulations were prepared with different ratios of PEG and Glycerin in the final fill formulation. The order of mixing was same as that mentioned in Example 6. All of the formulations yielded clear solutions where the Arsenic Trioxide was completely solubilized in the formulation. There was slight yellowish color formation which could be easily prevented by the addition of antioxidant such as BHT.

All four of the above solutions were evaluated to see if they would precipitate in the GI tract. One ml of the formulation was added to 900 ml of simulated gastric fluid. There was no evidence of any precipitation.

Example 8: pH Adjustment of the Concentrated Arsenic Trioxide Solution

TABLE 12

| Sr. No. | Ingredient Name | Trial 36 |
|---|---|---|
| 1 | Sodium Hydroxide Solution | 3M |
|  | Qty. of NaOH solution taken | 20 ml |
| 2 | Qty. of NaOH present in solution | 2.40 gm |
| 3 | Addition of Arsenic Trioxide | 4.00 gm |
|  | Stirring time | 30 mins |
|  | Observation/Description | Clear solution observed |
|  | Observed pH | 14.16 |
| 4 | Addition of 6M HCl solution under stirring (HCl solution consumed to attain the pH) | 6.6 ml |
|  | Observed pH | 7.91 |
|  | Observation/Description | Solution was clear up to pH 9.58, it started becoming hazy when pH reaches to 8.5. At pH 7.91 it started precipitating out. |

Process: A concentrated solution of 200 mg/ml of Arsenic Trioxide was prepared using 3M NaOH solution. The pH of the solution was 14.16. This solution was partially neutralized by adding dropwise 6 M HCl. The solution remained crystal clear till the pH reached 9.58. Thereafter, the solution became hazy (but no visual signs of precipitation) when the pH reached 8.5. Subsequently, the Arsenic Trioxide started precipitating out when the solution reached pH 7.91.

Example 9: Preparation of Fill Matrix with pH Adjusted Concentrated Arsenic Trioxide Solution

TABLE 13

| Sr. No. | Ingredient Name | Trial 37 | Trial 38A | Trial 38B |
|---|---|---|---|---|
| 1 | Sodium Hydroxide Solution | 3M | 3M | 3M |
|  | Qty. of NaOH solution taken | 20 ml | 20 ml | 20 ml |
| 2 | Qty. of NaOH present in solution | 2.40 gm | 2.40 gm | 2.40 gm |
| 3 | Addition of Arsenic Trioxide | 4.00 gm | 4.00 gm | 4.00 gm |
|  | Stirring time | 30 mins | 30 mins | 30 mins |
|  | Observation/Description | Clear solution observed | Clear solution observed | Clear solution observed |
|  | Observed pH | 13.3 | 13.17 | 13.17 |
| 4 | Addition of 6M HCl solution under stirring (HCl solution consumed to attain the pH) | 3.5 ml | 5.5 ml | 5.5 ml |
|  | Observed pH | 10.04 | 9.07 | 9.07 |
|  | Observation/Description | No precipitation. Clear solution | No precipitation. Clear solution | No precipitation. Clear solution |
|  | Part-1 | | | |
| 5 | Take Arsenic Trioxide solution (after pH adjustment) | 2 ml (pH 10.04) | 2 ml (pH 9.07) | 2 ml (pH 9.07) 400 mg |
| 6 | Added PEG 400 | 18 ml | 18 ml | — |
| 6 | Added PEG 400 containing 0.2 % BHT | — | — | 18 ml |
|  | Stirring time | 30 mins | 30 mins | 30 mins |
|  | pH | 12.08 | 12.14 | 12.14 |
|  | Observation/Description | Slight Hazy solution | No precipitation. Clear solution | No precipitation. Clear solution |
|  | Observation/Description (After 24 hours) | Very slight yellowish hazy solution | Clear solution observed | Clear solution observed |

TABLE 13-continued

| Sr. No. | Ingredient Name | Trial 37 | Trial 38A | Trial 38B |
|---|---|---|---|---|
| | Part-2 | | | — |
| I | Take Arsenic Trioxide solution (after pH adjustment) | 2 ml (pH 10.04) | 2 ml (pH 9.07) | |
| II | Added Glycerin (1 part) | 1.8 ml | 1.8 ml | |
| III | Added PEG 400 (9 part) | 16.2 ml | 16.2 ml | |
| Stirring time | | 30 mins | 30 mins | |
| pH | | 10.75 | 10.3 | |
| Observation/Description | | No precipitation. Clear solution | No precipitation. Clear solution | |
| Observation/Description (After 24 hours) | | Not precipitated. Clear solution | Not precipitated. Clear solution | |

Process: pH of the Concentrated solution of Arsenic Trioxide is first adjusted by the addition of HCl. In Part 1 of the Trial 37 and 38A; part of the pH adjusted Arsenic Trioxide solution is mixed with PEG 400. Clear to slight hazy fill solution is obtained in Trial 37 but a clear solution is obtained with Trial 38A. Upon storage, the solutions of Part 1 develop a slight yellow tint. This development of yellow tint can be prevented by adding an antioxidant to PEG 400 as mentioned in the Exemplary Trial 38B. However, in Part 2 of the trial, when pH adjusted concentrated Arsenic Trioxide solution is premixed with glycerin, and then added to PEG 400, mixed for 30 min—a stable crystal-clear solution is obtained.

Example 10: Order of Addition of Ingredients

TABLE 14A

| Sr. No. | Ingredient Name | Trial 39 | Trial 40 |
|---|---|---|---|
| 1 | Sodium Hydroxide Solution preparation | 6M | 6M |
| 2 | Qty. of NaOH solution taken | 10 ml | 10 ml |
| 3 | Qty. of NaOH present in solution | 2.40 gm | 2.40 gm |
| 4 | Addition of Arsenic Trioxide | 5.4 gms | 5.4 gms |
| Stirring time | | 30 mins | 30 mins |
| Observation/Description | | Clear Colorless Colorless Solution | Clear Colorless Colorless Solution |
| Observed pH | | 12.72 | 12.47 |
| 5 | Addition of 6M HCl solution under stirring | 7.0 ml | 7.0 ml |
| Observed pH | | 9.34 | 9.28 |
| Final Conc of Arsenic | | 317.6 mg/ml | 317.6 mg/ml |
| Observation/Description | | Turbid Solution | Turbid Solution |
| 5A | Take entire Arsenic Trioxide solution (after pH adjustment) | 17 ml (pH 9.34) corresponds to 20 mg/ml | 17 ml (pH 9.28) corresponds to 20 mg/ml |
| 6 | Added Glycerine (1 part) | 24.3 ml | — |
| 6 | Added Propylene glycol (1 part) | — | 24.3 ml |
| Stirring Time | | 30 mins | 30 mins |
| Observation/Description | | Transluscent Solution with slight precipitation | Transluscent Solution with slight precipitation |
| 7 | Added PEG 600 (9 part) | 228.7 ml | 228.7 ml |
| Stirring time | | 30 mins | 30 mins |
| pH | | 10.07 | 10.6 |
| Observation/Description | | Clear Colorless Solution | Clear Colorless Solution with slight undissolved particles were observed |
| Observation/Description (After 24 hours) | | Clear Colorless Solution | Clear Colorless Solution |
| Observation/Description (After 72 hours) | | Clear Colorless Solution | Clear Colorless Solution |

TABLE 14A-continued

| Sr. No. | Ingredient Name | Trial 39 | Trial 40 |
|---|---|---|---|
| 8 | Qty. of Above solution taken | 1 ml | 1 ml |
| 9 | DI water taken | 9 ml | 9 ml |
| pH | | 8.85 | 9.05 |
| Observation/Description | | Clear Colorless Solution | Clear Colorless Solution |

Example 10: Order of Addition of Ingredients

TABLE 14B

| Sr. No. | Ingredient Name | Trial 41 | Trial 42 |
|---|---|---|---|
| 1 | Sodium Hydroxide Solution preparation | 6M | 6M |
| 2 | Qty. of NaOH solution taken | 10 ml | 10 ml |
| 3 | Qty. of NaOH present in solution | 2.40 gm | 2.40 gm |
| 4 | Addition of Arsenic Trioxide | 5.4 gms | 5.4 gms |
| Stirring time | | 30 mins | 30 mins |
| Observation/Description | | ClearColorless Colorless Solution | ClearColorless Colorless Solution |
| Observed pH | | 12.45 | 12.47 |
| 5 | Glycerin | 24.3 ml | |
| 5 | Propylene glycol | | 24.3 ml |
| 6 | Addition of 6M HCl solution under stirring | 7.0 ml | 7.0 ml |
| Observed pH | | 9.02 | 9.28 |
| Final Conc of Arsenic | | 130.75 mg/ml | 130.75 mg/ml |
| Observation/Description | | No turbidity, clear colorless solution | No turbidity, clear colorless solution |
| 7 | Added PEG 600 (9 part) | 228.7 ml | 228.7 ml |
| Stirring time | | 30 mins | 30 mins |
| pH | | 10.2 | 10.6 |
| Observation/Description (After 24 hours) | | Clear Colorless Solution | Clear Colorless Solution |
| Observation/Description (After 72 hours) | | Clear Colorless Solution | Clear Colorless Solution |
| 8 | Qty. of Above solution taken | 1 ml | 1 ml |
| 9 | DI water taken | 9 ml | 9 ml |
| pH | | 9.06 | 9.05 |
| Observation/Description | | Clear Colorless Solution | Clear Colorless Solution |

Process for Trials 39 and 40

1. In both trials, Arsenic Trioxide solution is prepared using 6M solution of sodium hydroxide.

2. The solutions are partially neutralized using hydrochloric acid solution.

3. In trial 39, glycerin and in trial 40, propylene glycol are added and mixed thoroughly.

4. Thereafter, Polyethylene glycol is added in both trials and mixed thoroughly. Clear colorless solution is obtained in Trial 39 whereas clear colorless solution with slight undissolved particles were observed in Trial 40. However, this solution completely clears up on standing.

5. Further, 1 ml of each solution is diluted by 9 ml of deionized (DI) water to check for precipitation or turbidity. Clear solution is obtained on dilution for trial 39. Few particles are observed initially for trial 40 which disappeared subsequently producing a clear colorless solution.

Process for Trials 41 and 42

1. In both trials, Arsenic Trioxide solution is prepared using 6M solution of sodium hydroxide.

2. In trial 41, glycerin and in trial 42, propylene glycol are added and mixed thoroughly.

3. The solutions are partially neutralized using hydrochloric acid solution.

4. Thereafter, Polyethylene glycol is added in both trials and mixed thoroughly. The samples of Trial 41 and 42 were clear instantaneously.

5. Further, 1 ml of each solution is diluted by 9 ml of water to check for precipitation or turbidity. Clear colorless solutions are obtained in both the trials.

Example 12: Exemplary Formulations of Fill Matrices Using Different Ratios of Sodium Hydroxide and Arsenic Trioxide

TABLE 16A

| Table 16A | | | | | | | |
|---|---|---|---|---|---|---|---|
| Sodium Hydroxide to Arsenic Trioxide Ratio of 0.25:1 | | | | | | | |
| Trial 43 | | 1M NaOH = 40 mg/ml | | | | | |
| | | Volume of NaOH | | | | | |
| | mg | 1M | 2M | 3M | 4M | 5M | 6M |
| Arsenic Trioxide | 5400 | 5400 | 5400 | 5400 | 5400 | 5400 | 5400 |
| NaOH | 1350 | 33.75 | 16.875 | 11.25 | 8.4375 | 6.75 | 5.625 |
| 70% Neutralization of NaOH by HCl | | | | | | | |
| | | 1M HCl | 2M HCl | 3M HCl | 4M HCl | 5M HCl | 6M HCl |
| HCl | | 23.625 | 11.8125 | 7.875 | 5.90625 | 4.725 | 3.9375 |
| Glycerine (ml) | 24.3 | 24.3 | 24.3 | 24.3 | 24.3 | 24.3 | 24.3 |
| PEG (ml) | 228.7 | 228.7 | 228.7 | 228.7 | 228.7 | 228.7 | 228.7 |
| Total Formulation (ml) | | 310.375 | 281.6875 | 272.125 | 267.3438 | 264.475 | 262.5625 |
| Final Conc of Arsenic Trioxide (mg/ml) | | 17.39831 | 19.17018 | 19.84382 | 20.19871 | 20.41781 | 20.56653 |
| Final water content in Formulation (% v/v) | | 18.4857 | 10.18416 | 7.02802 | 5.365283 | 4.338784 | 3.64199 |
| Final Glycerin content in Formulation (% v/v) | | 7.829239 | 8.626581 | 8.92972 | 9.089421 | 9.188014 | 9.254939 |

| Table 16 B | | | | | | | |
|---|---|---|---|---|---|---|---|
| Sodium Hydroxide to Arsenic Trioxide Ratio of 0.5:1 | | | | | | | |
| Trial 44 | | 1M NaOH = 40 mg/ml | | | | | |
| | | Volume of NaOH | | | | | |
| | mg | 1M | 2M | 3M | 4M | 5M | 6M |
| ARSENIC TRIOXIDE | 5400 | 5400 | 5400 | 5400 | 5400 | 5400 | 5400 |
| NaOH | 2700 | 67.5 | 33.75 | 22.5 | 16.875 | 13.5 | 11.25 |
| 70% Neutralization of NaOH by HCl | | | | | | | |
| | | 1M HCl | 2M HCl | 3M HCl | 4M HCl | 5M HCl | 6M HCl |
| HCl | | 47.25 | 23.625 | 15.75 | 11.8125 | 9.45 | 7.875 |
| Glycerine (ml) | 24.3 | 24.3 | 24.3 | 24.3 | 24.3 | 24.3 | 24.3 |
| PEG (ml) | 228.7 | 228.7 | 228.7 | 228.7 | 228.7 | 228.7 | 228.7 |
| Total Formulation (ml) | | 367.75 | 310.375 | 291.25 | 281.6875 | 275.95 | 272.125 |
| Final Conc of Arsenic Trioxide (mg/ml) | | 14.68389 | 17.39831 | 18.54077 | 19.17018 | 19.56876 | 19.84382 |
| Final water content in Formulation (% v/v) | | 31.20326 | 18.4857 | 13.13305 | 10.18416 | 8.316724 | 7.02802 |

Table 16 B

| | | | | | | |
|---|---|---|---|---|---|---|
| Final Glycerin content in Formulation (% v/v) | 6.60775 | 7.829239 | 8.343348 | 8.626581 | 8.805943 | 8.92972 |

Table 16 C

Sodium Hydroxide to Arsenic Trioxide Ratio of 0.75:1

| Trial 45 | | 1M NaOH = 40 mg/ml | | | | | |
|---|---|---|---|---|---|---|---|
| | | | Volume of NaOH | | | | |
| | mg | 1M | 2M | 3M | 4M | 5M | 6M |
| Arsenic Trioxide | 5400 | 5400 | 5400 | 5400 | 5400 | 5400 | 5400 |
| NaOH | 4050 | 101.25 | 50.625 | 33.75 | 25.3125 | 20.25 | 16.875 |
| | | 70% Neutralization of NaOH by HCl | | | | | |
| | | 1M HCl | 2M HCl | 3M HCl | 4M HCl | 5M HCl | 6M HCl |
| HCl | | 70.875 | 35.4375 | 23.625 | 17.71875 | 14.175 | 11.8125 |
| Glycerine (ml) | 24.3 | 24.3 | 24.3 | 24.3 | 24.3 | 24.3 | 24.3 |
| PEG (ml) | 228.7 | 228.7 | 228.7 | 228.7 | 228.7 | 228.7 | 228.7 |
| Total Formulation (ml) | | 425.125 | 339.0625 | 310.375 | 296.0313 | 287.425 | 281.6875 |
| Final Conc of Arsenic Trioxide (mg/ml) | | 12.70215 | 15.92627 | 17.39831 | 18.24132 | 18.78751 | 19.17018 |
| Final water content in Formulation (% v/v) | | 40.48809 | 25.38249 | 18.4857 | 14.53605 | 11.97704 | 10.18416 |
| Final Glycerin content in Formulation (% v/v) | | 5.715966 | 7.16682 | 7.829239 | 8.208593 | 8.454379 | 8.626581 |

TABLE 16D

Sodium Hydroxide to Arsenic Trioxide Ratio of 1:1

| Trial 46 | | 1M NaOH = 40 mg/ml | | | | | |
|---|---|---|---|---|---|---|---|
| | | | Volume of NaOH (ml) | | | | |
| | mg | 1M | 2M | 3M | 4M | 5M | 6M |
| Arsenic Trioxide | 5400 | 5400 | 5400 | 5400 | 5400 | 5400 | 5400 |
| NaOH | 5400 | 135 | 67.5 | 45 | 33.75 | 27 | 22.5 |
| | | 70% Neutralization of NaOH by HCl | | | | | |
| | | 1M HCl | 2M HCl | 3M HCl | 4M HCl | 5M HCl | 6M HCl |
| HCl | | 94.5 | 47.25 | 31.5 | 23.625 | 18.9 | 15.75 |
| Glycerine (ml) | 24.3 | 24.3 | 24.3 | 24.3 | 24.3 | 24.3 | 24.3 |
| PEG (ml) | 228.7 | 228.7 | 228.7 | 228.7 | 228.7 | 228.7 | 228.7 |
| Total Formulation (ml) | | 482.5 | 367.75 | 329.5 | 310.375 | 298.9 | 291.25 |

TABLE 16D-continued

| | | | | | | |
|---|---|---|---|---|---|---|
| Final Conc of Arsenic Trioxide (mg/ml) | 11.19171 | 14.68389 | 16.38847 | 17.39831 | 18.06624 | 18.54077 |
| Final water content in Formulation (% v/v) | 47.56477 | 31.20326 | 23.217 | 18.4857 | 15.35631 | 13.13305 |
| Final Glycerin content in Formulation (% v/v) | 5.036269 | 6.60775 | 7.37481 | 7.829239 | 8.129809 | 8.343348 |

Process for Exemplary Trials 43-46
1. Prepare various molar solutions of sodium hydroxide and hydrochloric acid.
2. Dissolve Arsenic Trioxide in sodium hydroxide solutions and mix thoroughly.
3. Add the required amount of Glycerin and mix thoroughly.
4. Add required amount of hydrochloric acid solution and mix thoroughly.
5. Finally add required amount of polyethylene glycol and mix thoroughly.

REFERENCES

Non-Patent Literature References

Loyer Annie-Florence, Medsenic Announces Positive Results of its Phase II Clinical Study with ARSCIMED® for the Treatment of Chronic Graft Versus Host Disease (cGvHD), businesswire, Mar. 29, 2021.

National Research Council (US) Committee on Medical and Biological Effects of Environmental Pollutants. Arsenic: Medical and Biologic Effects of Environmental Pollutants. Washington (DC): National Academies Press (US); 1977. 2, Chemistry of Arsenic. Available from: NCBI NLM NIH books.

Kumana C R, Mak R, Kwong Y L, Gill H. Resurrection of Oral Arsenic Trioxide for Treating Acute Promyelocytic Leukaemia: A Historical Account From Bedside to Bench to Bedside. Front Oncol. 2020; 10:1294. Published 2020 Aug. 4. doi:10.3389/fonc.2020.01294.

Hong-Hu Zhu, De-Pei Wu, Jie Jin, Jian-Yong Li, Jun Ma, Jian-Xiang Wang, Hao Jiang, Sai-Juan Chen, and Xiao-Jun Huang Journal of Clinical Oncology 2013 31:33, 4215-4221.

"Arsenic Trioxide" on the chem.libretexts website.

Gullapalli R P. Soft gelatin capsules (softgels). J Mann Sci. 2010 October; 99(10):4107-48, doi: 10.1002/jps.22151. PMID: 20737624.

Patent References Cited

1. U.S. Pat. No. 5,200,191A
2. U.S. Pat. No. 6,340,473B1
3. U.S. Pat. No. 7,521,071B2
4. U.S. Pat. No. 10,111,836B2
5. U.S. Pat. No. 10,653,628B2
6. U.S. Pat. No. 10,493,099B2
7. EP3106169B1

What is claimed is:

1. A pharmaceutical formulation comprising:
a liquid comprising arsenic trioxide, a solubilizing agent, a fill material, a water, and a glycerin or a propylene glycol;
wherein the liquid contains from 0.1-10 weight % of the arsenic trioxide dissolved in the liquid, based on a total weight of the liquid;
wherein the liquid contains the solubilizing agent from 0.1 part to 2.0 parts per part of arsenic trioxide by weight, and the solubilizing agent is selected from the group consisting of barium hydroxide, sodium hydroxide, potassium hydroxide, sodium metasilicate, calcium hydroxide, trisodium phosphate, potassium carbonate, sodium carbonate, ammonium hydroxide, diethylamine, triethylamine, tromethamine, picoline, dicyclohexylamine, N,N'-dibenzyl-ethylenediamine, amino acids, salts of amino acids, and combinations thereof;
wherein the liquid contains at least 60 weight % of the fill material, based on the total weight of the liquid, and the fill material is selected from the group consisting of PEG 200, PEG 300, PEG 400, PEG 600, PEG 800, PEG 1000, poloxamers, ethanol, dimethyl isosorbide, 2-(2-ethoxyethoxy)ethanol, lauroyl polyoxyl-32 glycerides, lauroyl macrogol-32 glycerides, stearoyl polyoxyl-32 glycerides, stearoyl macrogol-32 glycerides, polyethylene glycol monostearate, oleoyl macrogol-6 glycerides, oleoyl polyoxyl-6 glycerides, linoleoyl polyoxyl-6 glycerides, linoleoyl macrogol-6 glycerides, and combinations thereof;
wherein the liquid contains not more than 20 weight % of the water, based on the total weight of the liquid;
wherein the liquid has a pH of 8-12.5; and
wherein the liquid contains a weight ratio of the water to the glycerin of from 5:1 to 1:10 or a weight ratio of the water to the propylene glycol of from 5:1 to 1:10, wherein the weight ratio of the water to the glycerin or the weight ratio of the water to the propylene glycol is sufficient to dissolve arsenic trioxide in the liquid without discoloration.

2. The pharmaceutical formulation of claim 1, further comprising:
a surfactant, an absorption enhancer, a crystal growth inhibitor, a cosolvent, an antioxidant, or combinations thereof.

3. The pharmaceutical formulation of claim 1, wherein the fill material is selected from the group consisting of PEG 200, PEG 300, PEG 400, PEG 600, PEG 800, PEG 1000, combinations thereof.

4. The pharmaceutical formulation of claim 1, wherein the solubilizing agent is selected from the group consisting of sodium hydroxide, potassium hydroxide, calcium hydroxide, and combinations thereof.

5. The pharmaceutical formulation of claim 1, wherein the solubilizing agent is sodium hydroxide in an amount selected from the group consisting of 0.1-2.0 parts per part of arsenic trioxide by weight, 0.25-1.625 parts per part of arsenic trioxide by weight, 0.4-1.375 parts per part of arsenic trioxide by weight, and 0.4-0.875 parts per part of arsenic trioxide by weight.

6. The pharmaceutical formulation of claim 1, further comprising a neutralizing agent selected from the group consisting of sulfuric acid, carbonic acid, phosphoric acid, nitric acid, hydrochloric acid, hydrobromic acid, hydrofluoric acid, Boric acid, acetic acid, citric acid, ascorbic acid, lactic acid, acetylsalicylic acid, and oxalic acid.

7. The pharmaceutical formulation of claim 1, further comprising hydrochloric acid and wherein the solubilizing agent is sodium hydroxide, and the hydrochloric acid is present in an amount of from 50-80% moles/moles of the sodium hydroxide.

8. The pharmaceutical formulation of claim 2, wherein the cosolvent is selected from the group consisting of diethylene glycol, sodium lactate, propane diol, and combinations thereof.

9. The pharmaceutical formulation of claim 2, wherein the antioxidant is selected from the group consisting of butylated hydroxy anisole, butylated hydroxy toluene, thioglycerol, monothioglycerol, lipoic acid, propyl gallate, methionine, cysteine, metabisulfites, sodium formaldehyde sulfoxylate, phenol-containing aromatic and aliphatic compounds, dihydrolipoic acid, and combinations thereof.

10. The pharmaceutical formulation of claim 2, wherein the surfactant, absorption enhancer, and crystal growth inhibitor are independently selected from the group consisting of sodium polyacrylate, polyvinyl pyrrolidone (PVP), macrogol 15 hydroxystearate, propylene glycol caprylate, polyoxyl 40 hydrogenated castor oil, and combinations thereof.

11. The pharmaceutical formulation of claim 1,
wherein the liquid contains from 0.2-5% weight of the arsenic trioxide dissolved in the liquid, based on a total weight of the liquid;
wherein the liquid contains the solubilizing agent from 0.4 parts to 0.875 parts per part of arsenic trioxide by weight;
wherein the liquid contains at least 70 weight % of the fill material, based on the total weight of the liquid;
wherein the liquid contains not more than 10 weight % of the water, based on the total weight of the liquid;
wherein the liquid has a pH of 8.0-9.5, and wherein the liquid does not contain more than 20% weight of glycerin or propylene glycol, based on the total weight of the liquid, wherein the liquid contains a weight ratio of the water to the glycerin of from 1:1 to 1:3; or, wherein the liquid contains a weight ratio of the water to the propylene glycol of from 1:1 to 1:3.

12. The pharmaceutical formulation of claim 11, wherein the solubilizing agent comprises sodium hydroxide, and wherein the fill material comprises a polyethylene glycol.

13. A soft capsule comprising:
a liquid comprising:
5-20 mg arsenic trioxide dissolved in the liquid;
2-17.5 mg of a solubilizing agent solution in the liquid, wherein the solubilizing agent is sodium hydroxide;
1-14 mg of a neutralizing agent solution in the liquid;
10-50 mg water in the liquid;
200-900 mg of a fill material in the liquid, wherein the fill material is a polyethylene glycol; and
20-150 mg glycerin in the liquid; and
wherein the weight of water to glycerin is sufficient to dissolve arsenic trioxide in the liquid without discoloration.

14. The soft capsule of claim 13, wherein the neutralizing agent is hydrochloric acid.

* * * * *